(12) United States Patent
McFarland, Jr.

(10) Patent No.: US 12,402,810 B2
(45) Date of Patent: *Sep. 2, 2025

(54) TRANSPORT GAIT AND GESTURE INTERPRETATION

(71) Applicant: TOYOTA MOTOR NORTH AMERICA, INC., Plano, TX (US)

(72) Inventor: Stephen Paul McFarland, Jr., Allen, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 989 days.

This patent is subject to a terminal disclaimer.

(21) Appl. No.: 17/505,349

(22) Filed: Oct. 19, 2021

(65) Prior Publication Data

US 2022/0031197 A1 Feb. 3, 2022

Related U.S. Application Data

(63) Continuation-in-part of application No. 16/837,984, filed on Apr. 1, 2020, now Pat. No. 11,163,372.

(51) Int. Cl.
*A61B 5/11* (2006.01)
*A61B 5/00* (2006.01)

(52) U.S. Cl.
CPC ............ *A61B 5/112* (2013.01); *A61B 5/1126* (2013.01); *A61B 5/7405* (2013.01); *A61B 5/742* (2013.01)

(58) Field of Classification Search
CPC ..... G06F 3/017; G06F 3/167; G06K 9/00791; G06K 9/00348; G06K 9/00355; B60R 11/04; G06Q 50/30; B60Q 1/50
See application file for complete search history.

(56) References Cited

U.S. PATENT DOCUMENTS

| 8,196,066 | B1 | 6/2012 | Ouyang et al. |
| 10,192,415 | B2 | 1/2019 | Heitz, III et al. |
| 10,233,021 | B1 | 3/2019 | Brady et al. |
| 10,395,457 | B2 | 8/2019 | Cooley |
| 2006/0001545 | A1 | 1/2006 | Wolf |
| 2015/0161836 | A1 | 6/2015 | Park et al. |
| 2015/0191178 | A1 | 7/2015 | Roy et al. |
| 2018/0141562 | A1 | 5/2018 | Singhal |
| 2018/0251122 | A1 | 9/2018 | Golston et al. |
| 2018/0290627 | A1 | 10/2018 | Hariri et al. |

(Continued)

FOREIGN PATENT DOCUMENTS

| CN | 105867371 A | 8/2016 |
| CN | 104149736 B | 11/2016 |

(Continued)

*Primary Examiner* — Pei Yong Weng

(57) ABSTRACT

An example operation includes one or more of receiving, by a computer associated with a transport, a gait of an individual from at least one sensor associated with the transport, validating, by the computer, the gait when the gait has corresponding frequency occurrence statistics above a predetermined gait threshold, responsive to the validating, providing, by the computer, access to the transport by the individual, receiving, by the computer, a sequence of gestures of the individual from the at least one sensor, wherein the sequence of gestures corresponds to a function, validating, by the computer, the sequence of gestures, and responsive to the validating, performing, by the computer, the function responsive to the sequence of gestures being recognized as a known match with a pattern stored in memory.

20 Claims, 16 Drawing Sheets

(56) References Cited

U.S. PATENT DOCUMENTS

2019/0051069 A1  2/2019  Cooley
2021/0224524 A1  7/2021  Liu et al.

FOREIGN PATENT DOCUMENTS

| CN | 206664342 U | 11/2017 |
| CN | 108688593 A | 10/2018 |
| DE | 102018119239 A1 | 2/2019 |
| EP | 3299228 A1 | 3/2018 |
| EP | 3492944 A1 | 6/2019 |
| KR | 20190106845 A | 9/2019 |
| WO | 2019151995 A1 | 8/2019 |

100

550

640

TRANSPORT GAIT AND GESTURE INTERPRETATION

BACKGROUND

Vehicles or transports, such as cars, motorcycles, trucks, planes, trains, etc., generally provide transportation needs to occupants and/or goods in a variety of ways. Functions related to transports may be identified and utilized by various computing devices, such as a smartphone or a computer.

SUMMARY

One example embodiment provides a method that includes one or more of receiving, by a computer associated with a transport, a gait of an individual from at least one sensor associated with the transport, validating, by the computer, the gait when the gait has corresponding frequency occurrence statistics above a predetermined gait threshold, responsive to the validating, providing, by the computer, access to the transport by the individual, receiving, by the computer, a sequence of gestures of the individual from at the at least one sensor, wherein the sequence of gestures corresponds to a function, validating, by the computer, the sequence of gestures, and responsive to the validating, performing, by the computer, the function responsive to the sequence of gestures being recognized as a known match with a pattern stored in memory.

Another example embodiment provides a transport that includes a processor and a memory, coupled to the processor. The memory includes instructions, that when executed by the processor are configured to perform one or more of receive a gait of an individual from at least one sensor associated with the transport, validate the gait when the gait has corresponding frequency occurrence statistics above a predetermined gait threshold, responsive to the validate, provide access to the transport by the individual, receive a sequence of gestures of the individual from at the at least one sensor, wherein the sequence of gestures corresponds to a function validate the sequence of gestures, and responsive to the validate, perform the function responsive to the sequence of gestures are recognized as a known match with a pattern stored in memory.

A further example embodiment provides a non-transitory computer readable medium comprising instructions, that when read by a processor, cause the processor to perform one or more of receiving, by a computer associated with a transport, a gait of an individual from at least one sensor associated with the transport, validating, by the computer, the gait when the gait has corresponding frequency occurrence statistics above a predetermined gait threshold, responsive to the validating, providing, by the computer, access to the transport by the individual, receiving, by the computer, a sequence of gestures of the individual from at the at least one sensor, wherein the sequence of gestures corresponds to a function, validating, by the computer, the sequence of gestures, and responsive to the validating, performing, by the computer, the function responsive to the sequence of gestures being recognized as a known match with a pattern stored in memory.

DETAILED DESCRIPTION

Figure 1A:
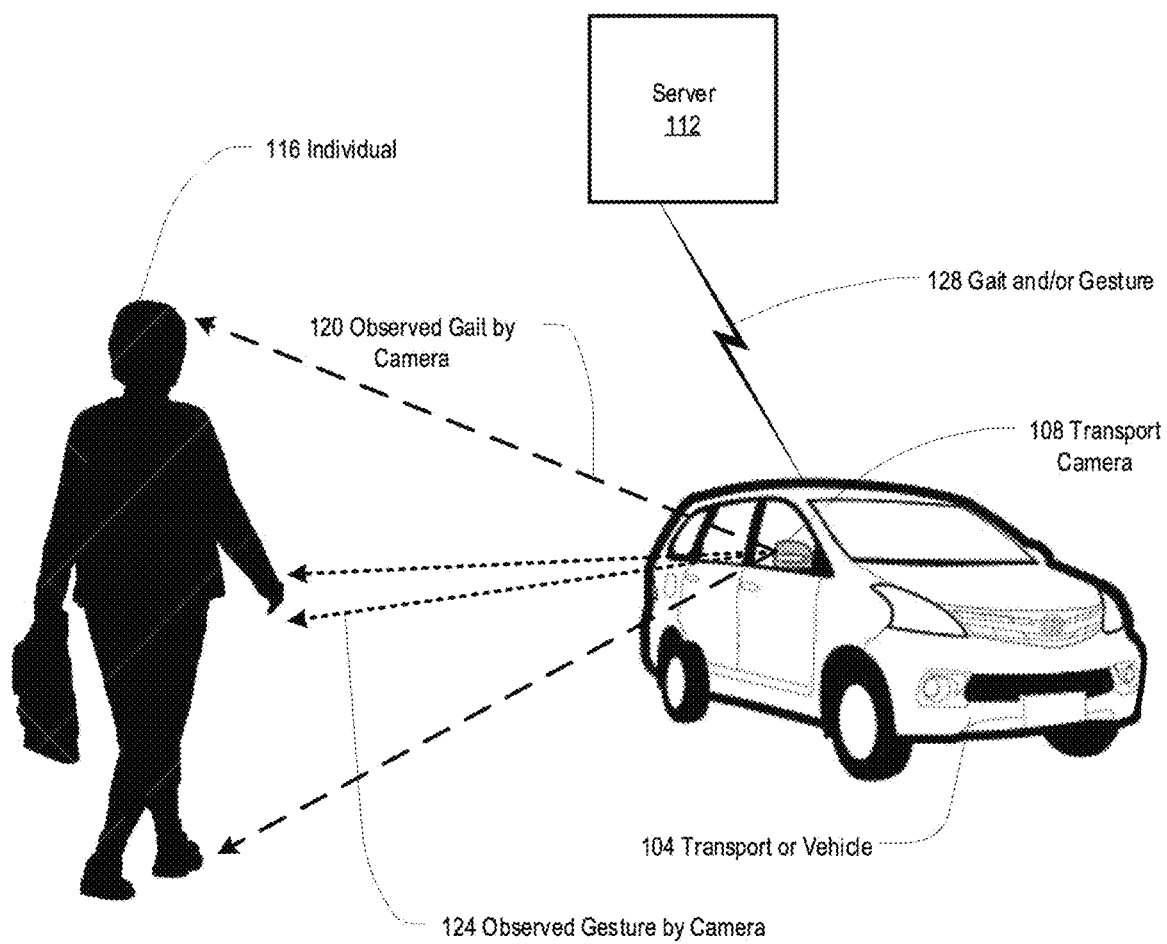
FIG. 1A illustrates an example diagram of observing a gait and a gesture from an individual by a transport, according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout least this specification refers to the fact that a particular feature, structure, or characteristic described in connection with the embodiment may be included in at one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments. In the diagrams, any connection between elements can permit one-way and/or two-way communication even if the depicted connection is a one-way or two-way arrow. In the current application, a transport may include one or more of cars, trucks, motorcycles, scooters, bicycles, boats, recreational vehicles, planes, and any object that may be used to transport people and or goods from one location to another.

In addition, while the term "message" may have been used in the description of embodiments, the application may be applied to many types of network data, such as, a packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

Example embodiments provide methods, systems, components, non-transitory computer readable media, devices, and/or networks, which provide at least one of: a transport (also referred to as a vehicle herein) a data collection system, a data monitoring system, a verification system, an authorization system and a vehicle data distribution system. The vehicle status condition data, received in the form of communication update messages, such as wireless data network communications and/or wired communication messages, may be received and processed to identify vehicle/transport status conditions and provide feedback as to the condition changes of a transport. In one example, a user profile may be applied to a particular transport/vehicle to authorize a current vehicle event, service stops at service stations, and to authorize subsequent vehicle rental services.

Within the communication infrastructure, a decentralized database is a distributed storage system, which includes multiple nodes that communicate with each other. A blockchain is an example of a decentralized database, which includes an append-only immutable data structure (i.e. a distributed ledger) capable of maintaining records between untrusted parties. The untrusted parties are referred to herein as peers, nodes or peer nodes. Each peer maintains a copy of the database records and no single peer can modify the database records without a consensus being reached among the distributed peers. For example, the peers may execute a consensus protocol to validate blockchain storage entries, group the storage entries into blocks, and build a hash chain via the blocks. This process forms the ledger by ordering the storage entries, as is necessary, for consistency. In a public or permissionless blockchain, anyone can participate without a specific identity. Public blockchains can involve cryptocurrencies and use consensus based on various protocols such as proof of work (PoW). On the other hand, a permissioned blockchain database provides a system, which can secure interactions among a group of entities which share a common goal, but which do not or cannot fully trust one another, such as businesses that exchange funds, goods, information, and the like. The instant application can function in a permissioned and/or a permissionless blockchain setting.

Smart contracts are trusted distributed applications which leverage tamper-proof properties of the shared or distributed ledger (i.e., which may be in the form of a blockchain) database and an underlying agreement between member nodes which is referred to as an endorsement or endorsement policy. In general, blockchain entries are "endorsed" before being committed to the blockchain while entries, which are not endorsed are disregarded. A typical endorsement policy allows smart contract executable code to specify endorsers for an entry in the form of a set of peer nodes that are necessary for endorsement. When a client sends the entry to the peers specified in the endorsement policy, the entry is executed to validate the entry. After validation, the entries enter an ordering phase in which a consensus protocol is used to produce an ordered sequence of endorsed entries grouped into blocks.

Nodes are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node which submits an entry-invocation to an endorser (e.g., peer), and broadcasts entry-proposals to an ordering service (e.g., ordering node). Another type of node is a peer node which can receive client submitted entries, commit the entries and maintain a state and a copy of the ledger of blockchain entries. Peers can also have the role of an endorser, although it is not a requirement. An ordering-service-node or orderer is a node running the communication service for all nodes, and which implements a delivery guarantee, such as a broadcast to each of the peer nodes in the system when committing entries and modifying a world state of the blockchain, which is another name for the initial blockchain entry, which normally includes control and setup information.

A ledger is a sequenced, tamper-resistant record of all state transitions of a blockchain. State transitions may result from smart contract executable code invocations (i.e., entries) submitted by participating parties (e.g., client nodes, ordering nodes, endorser nodes, peer nodes, etc.). An entry may result in a set of asset key-value pairs being committed to the ledger as one or more operands, such as creates, updates, deletes, and the like. The ledger includes a blockchain (also referred to as a chain), which is used to store an immutable, sequenced record in blocks. The ledger also includes a state database, which maintains a current state of the blockchain. There is typically one ledger per channel. Each peer node maintains a copy of the ledger for each channel of which they are a member.

A chain is an entry log, which is structured as hash-linked blocks, and each block contains a sequence of N entries where N is equal to or greater than one. The block header includes a hash of the block's entries, as well as a hash of the prior block's header. In this way, all entries on the ledger may be sequenced and cryptographically linked together. Accordingly, it is not possible to tamper with the ledger data without breaking the hash links. A hash of a most recently added blockchain block represents every entry on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain entry log. Because the current state represents the latest key values known to a channel, it is sometimes referred to as a world state. Smart contract executable code invocations execute entries against the current state data of the ledger. To make these smart contract executable code interactions efficient, the latest values of the keys may be stored in a state database. The state database may be simply an indexed view into the chain's entry log, it can therefore be regenerated from the chain at any time. The state database may automatically be recovered (or generated if needed) upon peer node startup, and before entries are accepted.

A blockchain is different from a traditional database in that the blockchain is not a central storage but rather a decentralized, immutable, and secure storage, where nodes must share in changes to records in the storage. Some properties that are inherent in blockchain and which help implement the blockchain include, but are not limited to, an immutable ledger, smart contracts, security, privacy, decentralization, consensus, endorsement, accessibility, and the like.

Transports are complex machines that include many functions related to transporting people and/or cargo. These functions include engine controls, climate controls, navigation controls, communication controls, and entertainment controls. These controls are generally arranged within reach of a driver's seating position in the transport, and therefore depend on an individual within the transport actuating the controls.

The present application describes a transport camera that detects a gait of an individual external to the transport. The gait allows identification of the individual, and enables detection of a gesture from the individual that causes the transport to perform one or more functions. In that way, a transport may activate one or more functions that would previously require the individual to be present and within the transport.

Example embodiments provide a way for providing a vehicle service to a particular vehicle and/or requesting user associated with a user profile that is applied to the vehicle. For example, a user may be the owner of a vehicle or the operator of a vehicle owned by another party. The vehicle may require service at certain intervals and the service needs may require authorization prior to permitting the services to be received. Also, service centers may offer services to vehicles in a nearby area based on the vehicle's current route plan and a relative level of service requirements (e.g., immediate, severe, intermediate, minor, etc.). The vehicle needs may be monitored via one or more sensors, which report sensed data to a central controller computer device in the vehicle, which in turn, is forwarded to a management server for review and action.

A sensor may be located on one or more of the interior of the transport, the exterior of the transport, on a fixed object apart from the transport, and on another transport near to the transport. The sensor may also be associated with the transport's speed, the transport's braking, the transport's acceleration, fuel levels, service needs, the gear-shifting of the transport, the transport's steering, and the like. The notion of a sensor may also be a device, such as a mobile device. Also, sensor information may be used to identify whether the vehicle is operating safely and whether the occupant user has engaged in any unexpected vehicle conditions, such as during the vehicle access period. Vehicle information collected before, during and/or after a vehicle's operation may be identified and stored in a transaction on a shared/distributed ledger, which may be generated and committed to the immutable ledger as determined by a permission granting consortium, and thus in a "decentralized" manner, such as via a blockchain membership group.

Each interested party (i.e., company, agency, etc.) may want to limit the exposure of private information, and therefore the blockchain and its immutability can limit the exposure and manage permissions for each particular user vehicle profile. A smart contract may be used to provide compensation, quantify a user profile score/rating/review, apply vehicle event permissions, determine when service is needed, identify a collision and/or degradation event, identify a safety concern event, identify parties to the event and provide distribution to registered entities seeking access to such vehicle event data. Also, the results may be identified, and the necessary information can be shared among the registered companies and/or individuals based on a "consensus" approach associated with the blockchain. Such an approach could not be implemented on a traditional centralized database.

Every autonomous driving system is built on a whole suite of software and an array of sensors. Machine learning, lidar projectors, radar, and ultrasonic sensors all work together to create a living map of the world that a self-driving car can navigate. Most companies in the race to full autonomy are relying on the same basic technological foundations of lidar+radar+cameras+ultrasonic, with a few notable exceptions.

In another embodiment, GPS, maps and other cameras and sensors are used in autonomous vehicles without lidar as lidar is often viewed as being expensive and unnecessary. Researchers have determined that stereo cameras are a low-cost alternative to the more expensive lidar functionality.

The instant application includes, in certain embodiments, authorizing a vehicle for service via an automated and quick authentication scheme. For example, driving up to a charging station or fuel pump may be performed by a vehicle operator, and the authorization to receive charge or fuel may be performed without any delays provided the authorization is received by the service station. A vehicle may provide a communication signal that provides an identification of a vehicle that has a currently active profile linked to an account that is authorized to accept a service which can be later rectified by compensation. Additional measures may be used to provide further authentication, such as another identifier may be sent from the user's device wirelessly to the service center to replace or supplement the first authorization effort between the transport and the service center with an additional authorization effort.

Data shared and received may be stored in a database, which maintains data in one single database (e.g., database server) and generally at one particular location. This location is often a central computer, for example, a desktop central processing unit (CPU), a server CPU, or a mainframe computer. Information stored on a centralized database is typically accessible from multiple different points. A centralized database is easy to manage, maintain, and control, especially for purposes of security because of its single location. Within a centralized database, data redundancy is minimized as a single storing place of all data also implies that a given set of data only has one primary record.

FIG. 1A illustrates an example diagram of observing a gait and a gesture from an individual by a transport 100, according to example embodiments. FIG. 1 illustrates a transport or vehicle 104 that includes one or more transport cameras 108. A transport 104 may include a front camera 108, a rear camera 108, and one or more side cameras 108. In one embodiment, side cameras 108 may be mounted within a side mirror assembly, although in other embodiments side cameras 108 may be mounted elsewhere. In one embodiment. a transport camera 108 may be part of a device associated with a transport 104 occupant. In another embodiment, the camera(s) 108 may be outside of the transport 104, such as in a smart-city environment.

Transport cameras 108 interface with one or more computers associated with the transport or vehicle 104. In one embodiment, the one or more computers (not shown) are within the transport 104. In another embodiment, the one or more computers may be outside the transport 104. In yet another embodiment, the one or more computers may be both inside and outside the transport 104. In one embodiment, the one or more computers may include a server 112 that receives a gait and/or gesture 128 of an individual 116. In one embodiment, the one or more computers may be within a cloud environment and communicably coupled to the transport 104. In another embodiment, the server 112 may be in the transport 104.

One or more transport cameras 108 observe a gait 120 of the individual 116. In one embodiment, the individual 116 may be within visual range of a transport camera 108, and may be stationary, approaching the transport 104, or moving away from the transport 104. In another embodiment, the individual 116 may not be within visual range of a transport camera 108, and the transport 104 instead receives a video or one or more images of the individual 116 over an interface such as a wireless interface. The video or one or more images may be received from one camera or multiple cameras. In one embodiment, the one or more computers may analyze the gait 120 only if the computers detect the individual 116 moving closer or approaching the vehicle or transport 104. In another embodiment, the one or more computers may analyze the gait 120 regardless of what the individual 116 is doing, but only analyze one or more gestures 124 if the computers detect the individual 116 moving closer or approaching the vehicle or transport 104.

The observed gait 120 may be compared with templates stored in a memory of the one or more computers of gaits of individuals 116 previously associated with a transport 104, such as a transport 104 owner, family member, or those who work within a same company that may own the transport 104. By observing movement of the individual 116 and motion of arms, legs, head, and torso with any associated rhythm or cadence, a pattern may be established that may be compared with other stored patterns to see if the observed gait 120 fits within one of the stored patterns. A match between the observed gait 120 and a stored pattern may identify the individual 116 and allow further observation of one or more gestures 124 by the individual 116. Finding such a match may constitute validating the gait 120.

Analyzing or determining the gait 120 of the individual 116 may include one or more of analyzing motion of the individual 116, a pace of the individual 116, leg movement of the individual 116, torso movement of the individual 116, arm movement of the individual 116, and head movement of the individual 116. In one embodiment, the gait 120 and the gesture 124 may be received by the transport camera 108 at a similar time. In another embodiment, the observed gesture 124 may be provided in response to an indication provided by the transport 104 to the individual 116. The indication includes at least one of flashing one or more lights of the transport 104, transmitting an audible message or tone from the transport 104 to the individual 116, and providing a notification to a device associated with the individual 116. The device may include any communication or computing device, including but not limited to a smart phone, smart watch, tablet, notebook computer, or any other form of communication or computing device. The indication may provide a notification to the individual 116 to provide one or more gestures 124 in order to activate or execute one or more functions of the transport 104. Lights of the transport 104 may include one or more of headlights, tail lights, interior lights, brake lights, or turn signals. In one embodiment, the audible message may be a spoken message in a language associated with either a location of the transport 104 or a language known to an individual 116 associated with the transport 104. In another embodiment, the audible message may be a spoken message in one or more languages spoken by one or more individuals 116 associated with the transport 104. A tone from the transport 104 may include any audible tones, including musical notes. The notification sent to the individual's 116 device may include one or more of an SMS message, an email, an image, or a video.

In one embodiment, the transport 104 may provide one or more of the gait 120 and the gesture 124 to the server 112. Either the transport 104 and/or the server 112 may maintain statistics associated with a frequency of occurrence of one or more of the gait 120 and the gesture 124. The statistics may provide a greater confidence with interpreting the gait 120 and/or the gesture 124. In one embodiment, the statistics may be increased in response to the one or more transport cameras 108 observing a gait 120 or gesture 124 that it has previously observed. In another embodiment, the one or more computers may act on an observed gesture 124 only if the observed gait 120 has corresponding statistics above a predetermined gait threshold. In yet another embodiment, the one or more computers may activate, enable, or utilize one or more functions of the transport 104 only if the observed gesture 124 has corresponding statistics above a predetermined gesture threshold.

The observed gesture 124 may be compared with templates stored in a memory of the one or more computers of gestures of individuals 116 previously associated with a transport 104, such as a transport 104 owner, family member, or those who work within a same company that may own the transport 104. By observing movement of the individual 116 and motion of fingers, hands, arms, legs, head, and torso with any associated rhythm or cadence, a pattern may be established that may be compared with other stored patterns to see if the observed gesture 124 fits within one of the stored patterns. A match between the observed gesture 124 and a stored pattern may identify one or more functions to be performed by the transport 124. Finding such a match may constitute validating the gesture 124.

The observed gesture by the transport camera 124 may result in one or more functions performed by the transport 104, and the one or more functions are based on the observed gesture 124. In one embodiment, the gesture 124 nay be received by the computer within a timeframe based on validating the gesture 124. The one or more functions may include one or more of unlocking a transport 104 door, starting an engine of the transport 104, utilizing a transport 104 heater or air conditioner, a summon function of the transport 104, and utilizing a transport 104 entertainment system. In one embodiment, an observed gesture 124 may activate, enable, or utilize more than one function (for example, starting an engine of the transport 104, unlocking a driver's door, and activating a seat or steering wheel heater). In another embodiment, different observed gestures 124 may result in different functions performed. In another embodiment, different observed gestures 124 from different individuals 116 may result in the same function(s) activated. For example, an individual 116 in a wheelchair may not have use of one or both legs to make gestures 124 with. Instead, once they are identified, the one or more computers may associate an arm or wheelchair movement as a same gesture 124 provided by a non-wheelchair bound individual's 116 legs.

In one embodiment, a hand gesture 124 may enable a first range of functions for the transport 104 (for example, engine-related functions), a finger gesture 124 may enable a second range of functions for the transport 104 (for example, lighting-related functions), and a combination of the hand gesture 124 and the finger gesture 124 enables a third range of functions for the transport 124 (for example, climate control functions). Other combinations of gestures may relate to other function groups. In one embodiment, a first gesture 124 may select a function group while a second gesture 124 may select a function within that function group. In another embodiment, a gesture 124 may stop a function already occurring (for example, turning an engine off after it has been running).

Figure 1B:
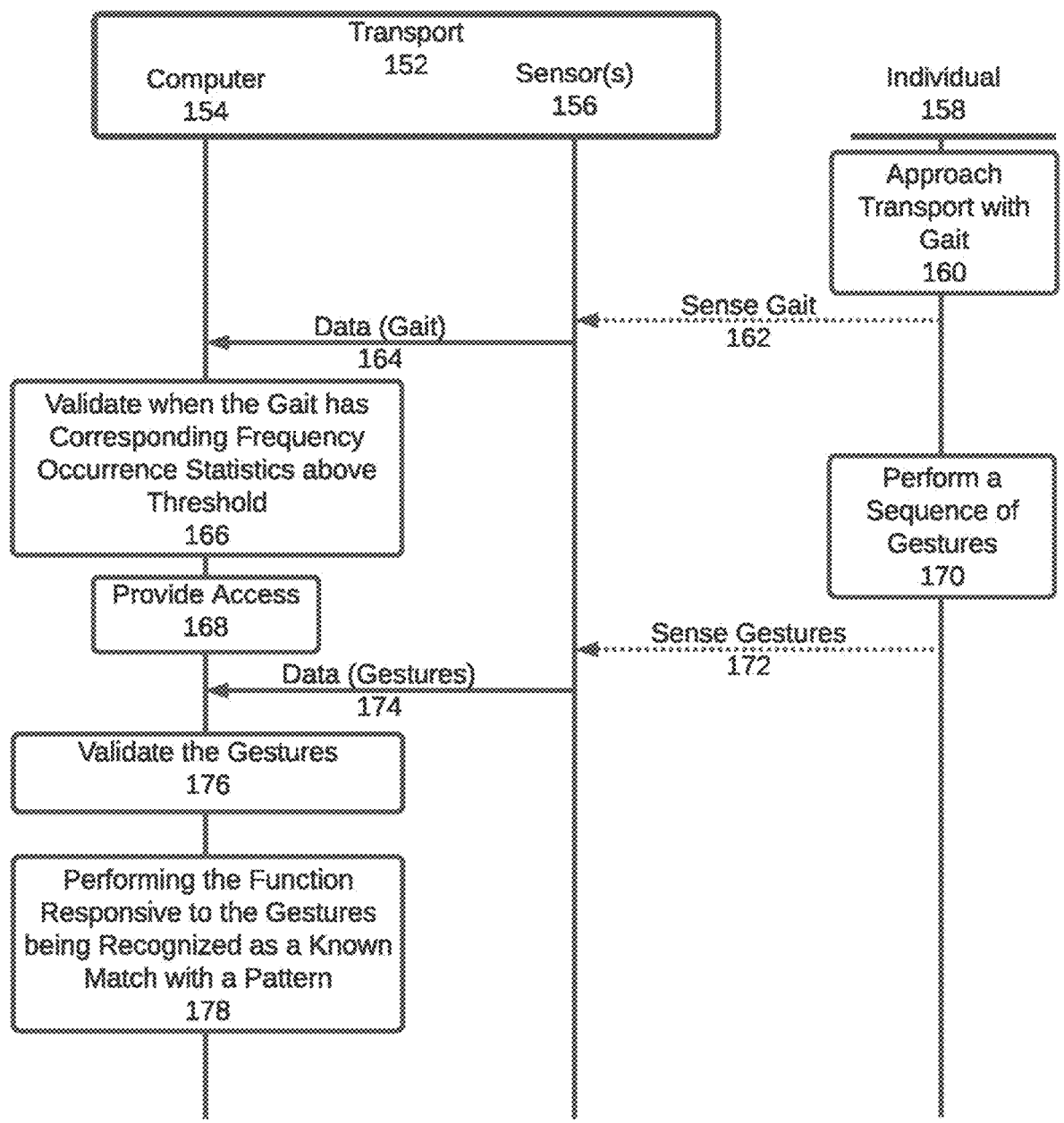
FIG. 1B illustrates an example flowchart of observing a gait and a sequence of gestures from an individual by a transport, according to example embodiments.

FIG. 1B illustrates an example flowchart of observing a gait and a sequence of gestures from an individual by a transport 150. The transport 152 may have a transport processor/computer 154, which may be referred to as an Electronic Control Module (ECM) by those familiar with the art. The transport processor may be associated with a transport computer that communicates with other processors in the transport via a Controller Area Network (CAN) bus. In one embodiment, the processing depicted herein may occur wholly or partially in the transport computer 154 or another processor associated with the transport, such as an Electronic Control Unit (ECU), a computer in the infotainment system of the transport, any device in the system, such as devices associated with one or more occupants of the transport (such as a mobile device), and a server (located inside the transport and/or outside). Communication between the server and the device associated with an occupant and the transport processor may occur through wired and/or wireless means, such as through normal wireless protocols commonly used in transports and is well known in the art.

The transport 152 may also contain sensors 156. The sensors may include, but are not limited to cameras, radar, ultrasonic, lidar, and may be located on the external or internal of the transport 152. Data collected by the sensors may be sent to the transport computer 154 of the transport 152 and may be processed therein.

An individual 158 may approach the transport 152. The individual, by nature, will have a gait 160. At least one sensor 156 on the transport may obtain data of the individual, including the gait of the individual. Sensors 156 on the transport may obtain data containing the individual, as the individual approaches the transport 162. The obtained data is sent from the sensor(s) 156 to the transport computer 154, such as through a Controller Area Network (CAN) bus. The CAN bus is a message-based protocol designed to allow the Electronic Control Units (ECUs) found in the transport, allowing communication through reliable methods. The current application, executing wholly or partially on the transport computer 154, analyzes the received data containing the obtained gait of the individual 164 to validate when the gait has a corresponding frequency occurrence statistic above a threshold 166 (as further described herein).

In one embodiment, a threshold is set for a matching gait of the individual 158. The threshold may be hardcoded into the current application and stored in memory, such as memory associated with the transport computer 154. The threshold may be set by one or more of the manufacturer of the transport, the dealer of the transport, and the like.

Matching of the gait in the received data 164 is performed by the current application executing on a processor, such as the transport processor 154. In one embodiment, data pertaining to the gait of one or more occupants associated with the transport are stored in memory, such as memory associated with the transport (e.g., the transport computer 154, or another memory in the transport), or memory associated with a server (not depicted) located outside of the transport 152. When the gait data is stored in an external server, messaging occurs between the transport 152 and the server through a network (not depicted). In one embodiment, the current application attempts to match the gait in the received data 164 with a stored gait of an occupant associated with the transport, such as the individual 158. The comparison must match the stored gait data above a threshold 166 for the processing of the current application to continue, otherwise, the processing stops. The received gait data 164 must have a corresponding frequency occurrence statistic at or above the threshold.

When the gait in the received data 164 has a corresponding frequency occurrence statistic at or above the threshold, the current application provides access to the transport 168, such as through the unlocking of one or more doors of the transport.

In another embodiment, when the sensors 156 determine that the individual 158 does not continue to approach the transport 152, but either passes the transport or turns away, the current application sends a command to lock the one or more previously opened doors of the transport 152. This may be determined by the object in the received data 164 getting smaller, in one embodiment. In another embodiment, object analysis functionality may determine whether the object is approaching or leaving the transport.

The individual 158 performs a sequence of gestures 170, wherein the sensor(s) send the data containing the sequence of gestures 172 to the transport computer 174. The transport computer 154, executing wholly or partially the current application, validates the sequence of gestures 176. In one embodiment, the observed sequence of gestures 174 may be compared with a database of gesture templates stored in a memory of the one or more computers of the transport 152, and a corresponding transport function to perform. The gesture templates contain data of gestures of individuals previously associated with a transport 152, such as a transport owner, family member, those who work within a same company that may own the transport or the like. By receiving data containing movement of the individual 158 such as motion of fingers, hands, arms, legs, head, and torso with any associated rhythm or cadence, a pattern may be established that may be compared with other the gesture templates to see if the observed sequence of gestures 170 matches with one of the stored gesture templates. A match between the observed sequence of gestures 170 and a stored gesture template may identify a transport function to be performed by the current application executing on the computer 154 of the transport 152. Finding such a match may constitute validating the gesture 176. In another embodiment, more than one function may be performed with a match of the sequence of gestures.

The observed sequence of gestures by the transport sensor 156 may result in one or more functions performed 178 by the transport 152, and the one or more functions are based on the observed sequence of gestures 174. In one embodiment, the sequence of gestures 170 may be received by the computer 154 within a timeframe based on validating the sequence of gestures 176. For example, the one or more functions may include one or more of unlocking a transport 152 door, starting an engine of the transport, utilizing a transport heater or air conditioner, utilizing a transport entertainment system, a summon function of the transport 152, and the like. In one embodiment, the observed sequence of gestures may activate, enable, or utilize more than one function (for example, starting an engine of the transport, unlocking a driver's door, and activating a seat or steering wheel heater). In another embodiment, different observed gestures may result in different functions performed.

In one embodiment, data containing the sequence of gestures is received at a device associated with the individual 158, such as a mobile phone, a wearable device, or the like. The received data may be received at the device that may execute the current application fully or partially. The received data is sent to the transport, such as for further processing, through wireless means, such as WIFI, or any other commonly used protocols supporting short-range wireless communication with a vehicle. Devices, such as mobile phones, have hardware that detects small movements of the device, such as an accelerometer and/or gyroscope components. The device may be able to detect gestures from the individual 158 with a high level of accuracy. For example, the individual has a mobile phone in their right hand, and the sequence of gestures is performed with the right hand. The components of the device detect the movements and one or more of the current application executing on the device and the current application executing on the transport computer 154 determine what the sequence of gestures are, such as by comparing the data received from the mobile device to a database of gestures templates, as further described herein. In one embodiment, the data of the sequence of gestures is sent to a server (not depicted), such as through a network. A processor associated with the server may execute wholly or partially the current application where the processing of the gait and/or sequence of gestures are processed. The corresponding transport function(s) determined by the received sequence of gestures are sent in a message to the transport 154 and received at the computer 154, accessible by the current application.

In one embodiment, the sequence of gestures enables a sequence of functions of the transport. For example, the sequence of gestures may be used as an authentication of the individual 158 to the transport 152. The sequence gestures received in the data 174 may be used to provide access to the transport and one basic function. For example, the individual 158 approaches the transport 152, and performs a sequence of gestures including holding up a right hand and waving the left hand while shaking the head. These gestures may be sequentially performed in one embodiment, and each specific gesture is received by the current application executing on the transport 152 and/or a device associated with the individual, such as a mobile device and/or a wearable device. The current application determines that these gestures relate to more than one function on the transport, such as unlocking one or more doors and starting the transport's engine. In another example, the three received gestures 174, when analyzed by the current application, map to the following functions: authenticate, unlock the doors, and have the transport maneuver to where the individual is current located. When the individual is not proximate to the transport, the current application executing in the processor in the device may detect the sequence of gestures, and wirelessly notify the transport through wireless protocols commonly used for short-range wireless communication between a device and the transport. The transport may determine the current location of the individual by utilizing location searches, such as through communication with the device with the individual associated with the current application where the geographic location of the device is currently, for example. In the current embodiment, the three gestures must be performed in order, or the authentication will not occur, and no functions will be executed on the transport.

In one embodiment, the validation of the sequence of gestures is performed by a server, such as a server located outside of transport 152, where communication between transport 152 and the server occurs through a network. The current application may wholly or partially execute on a processor of the server. The validation of the gait and/or the sequence of gestures are performed by the current application executing a device associated with an individual, such as mobile device. The gait and/or gesture data 164/174 is sent to the server through wireless communication, where the current application executing on a processor of the server validates that the gait and/or the sequence of gestures and are mapped successfully to at least one function of the transport. In one embodiment, the processing of the sequence of gestures 178 is only allowed once the gait of the individual is validated 166. Once the sequence of gestures is validated, the server provides access to a structure, such as another transport, a building (such as an office, a residence), and the like. This may occur by the sending of messages/commands to a network that forwards the message to the location through wired or wireless means. In one embodiment, a device associated with the structure may receive data containing a command to provide access to the structure by the individual, such as the unlocking of one or more doors at the structure. In one embodiment, the time that the structure is unlocked may be sent from transport 152 where the amount of time pertains to how far the transport is currently away from the structure. The transport may interwork with mapping data located inside the transport 152, such as in a navigation application on the transport, or outside the transport, such as in a server. Through this interaction, the current application determines the amount of time to destination. This time to destination is sent in one or more to the server and the structure through wireless communication, in one embodiment.

Figure 2A:
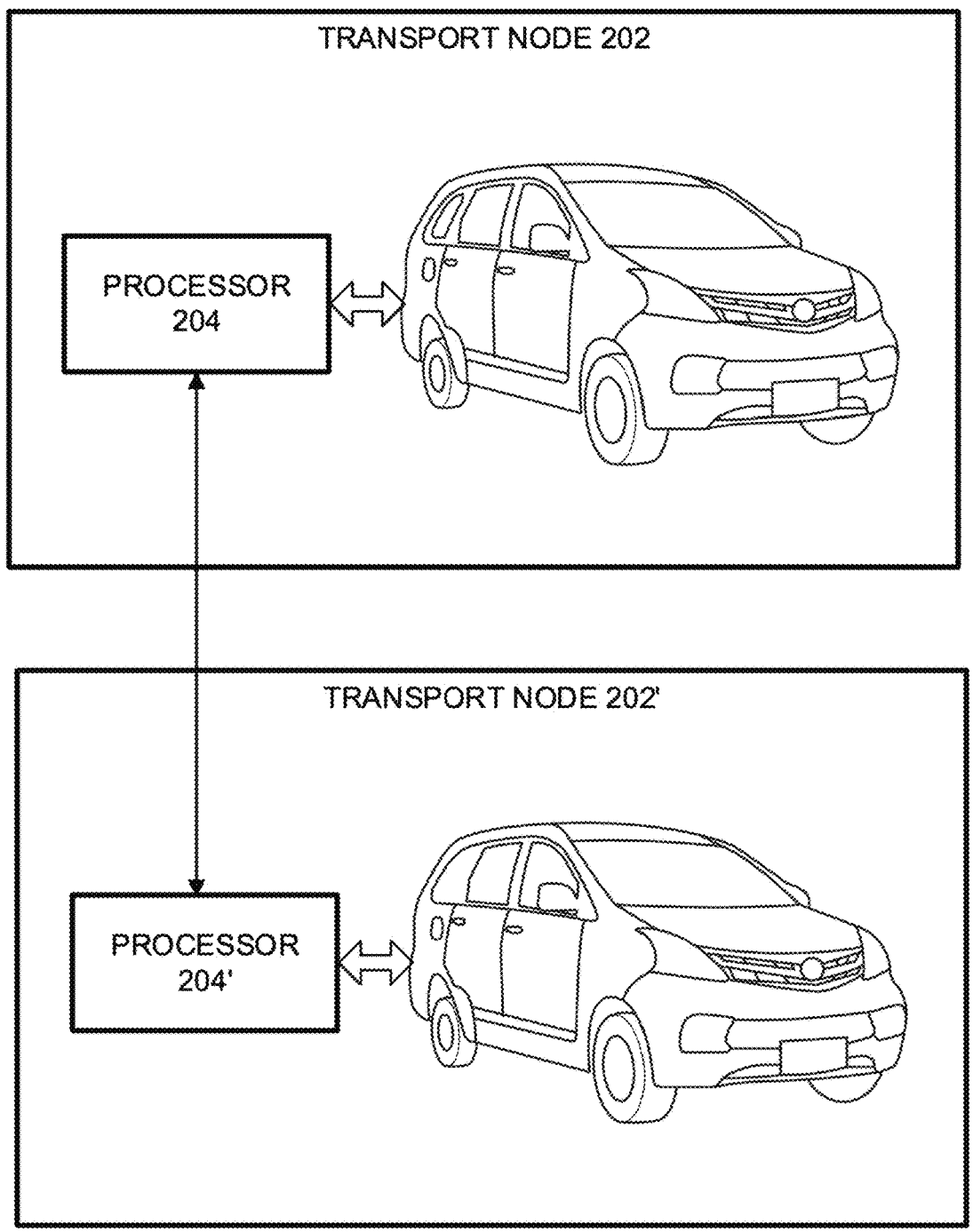
FIG. 2A illustrates a transport network diagram, according to example embodiments.

FIG. 2A illustrates a transport network diagram 200, according to example embodiments. The network comprises elements including a transport node 202 including a processor 204, as well as a transport node 202' including a processor 204'. The transport nodes 202, 202' communicate with one another via the processors 204, 204', as well as other elements (not shown) including transceivers, transmitters, receivers, storage, sensors, and other elements capable of providing communication. The communication between the transport nodes 202, 202' can occur directly, via a private and/or a public network (not shown) or via other transport nodes and elements comprising one or more of a processor, memory, and software. Although depicted as single transport nodes and processors, a plurality of transport nodes and processors may be present. One or more of the applications, features, steps, solutions, etc., described and/or depicted herein may be utilized and/or provided by the instant elements.

Figure 2B:
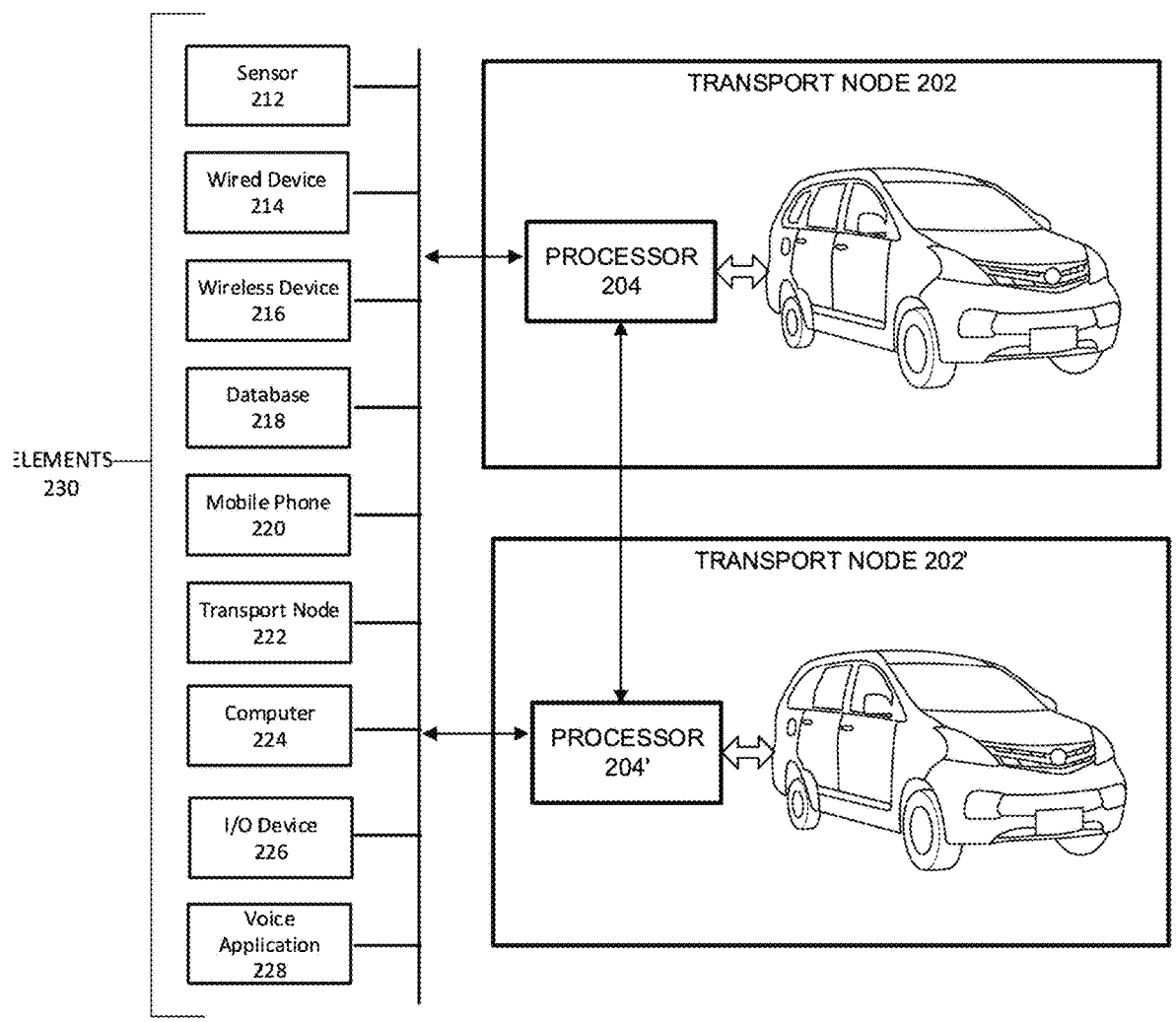
FIG. 2B illustrates another transport network diagram, according to example embodiments.

FIG. 2B illustrates another transport network diagram 210, according to example embodiments. The network comprises elements including a transport node 202 including a processor 204, as well as a transport node 202' including a processor 204'. The transport nodes 202, 202' communicate with one another via the processors 204, 204', as well as other elements (not shown) including transceivers, transmitters, receivers, storage, sensors, and other elements capable of providing communication. The communication between the transport nodes 202, 202' can occur directly, via a private and/or a public network (not shown) or via other transport nodes and elements comprising one or more of a processor, memory, and software. The processors 204, 204' can further communicate with one or more elements 230 including sensor 212, wired device 214, wireless device 216, database 218, mobile phone 220, transport node 222, computer 224, I/O device 226 and voice application 228. The processors 204, 204' can further communicate with elements comprising one or more of a processor, memory, and software.

Although depicted as single transport nodes, processors and elements, a plurality of transport nodes, processors and elements may be present. Information or communication can occur to and/or from any of the processors 204, 204' and elements 230. For example, the mobile phone 220 may provide information to the processor 204, which may initiate the transport node 202 to take an action, may further provide the information or additional information to the processor 204' which may initiate the transport node 202' to take an action, may further provide the information or additional information to the mobile phone 220, the transport node 222, and/or the computer 224. One or more of the applications, features, steps, solutions, etc., described and/or depicted herein may be utilized and/or provided by the instant elements.

Figure 2C:
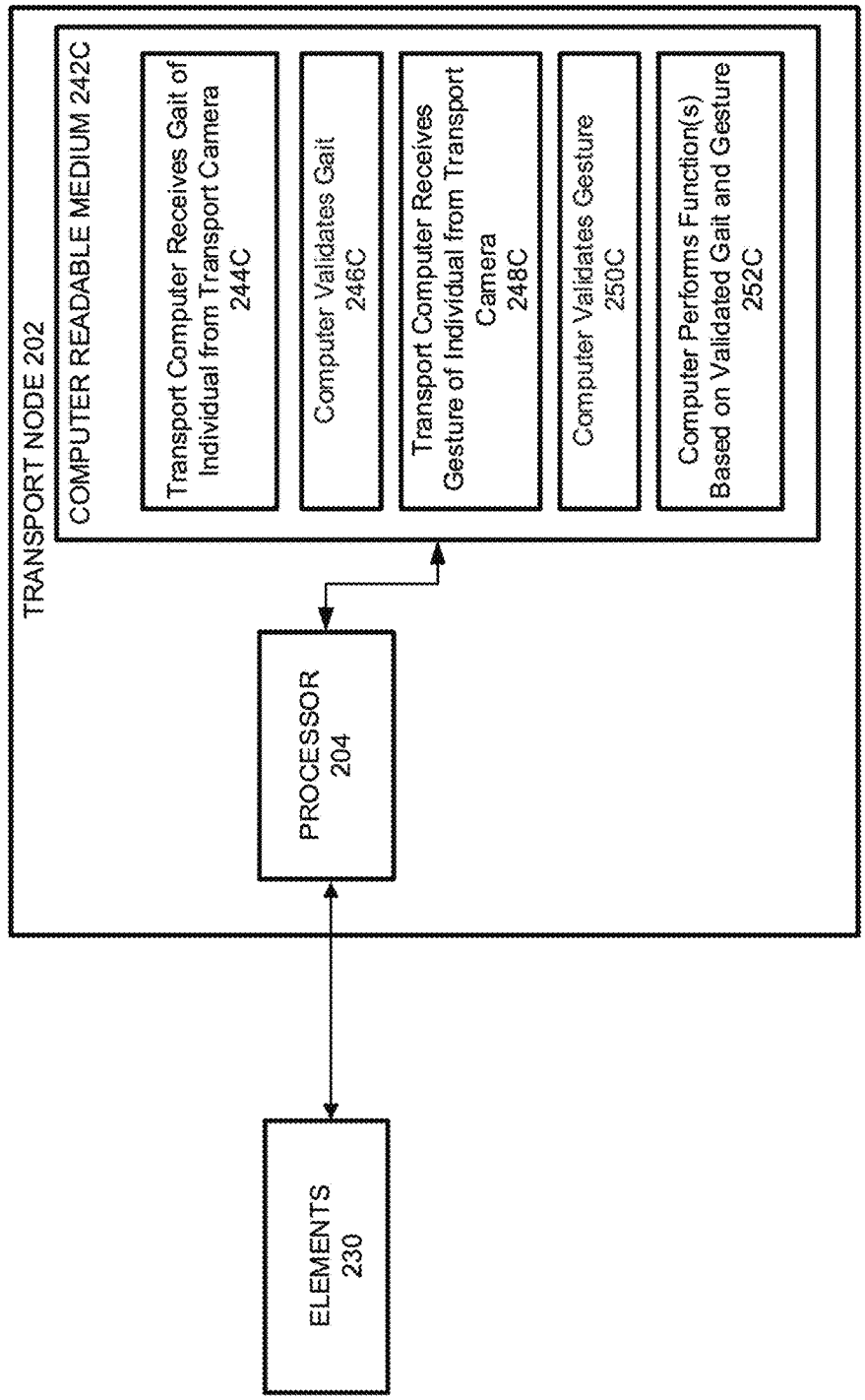
FIG. 2C illustrates yet another transport network diagram, according to example embodiments.

FIG. 2C illustrates yet another transport network diagram 240, according to example embodiments. The network comprises elements including a transport node 202 including a processor 204 and a non-transitory computer readable medium 242C. The processor 204 is communicably coupled to the computer readable medium 242C and elements 230 (which were depicted in FIG. 2B).

The processor 204 performs one or more of the following steps. At block 244C, the transport computer receives a gait 120 of an individual from a transport camera 108. At block 246C, the computer validates the gait 120. At block 248C, the transport computer receives a gesture 124 of the individual from the transport camera 108. At block 250C, the computer validates the gesture 124. At block 252C, the computer performs one or more functions based on the validated gait 120 and gesture 124.

The processors and/or computer readable media may fully or partially reside in the interior or exterior of the transport nodes. The steps or features stored in the computer readable media may be fully or partially performed by any of the processors and/or elements in any order. Additionally, one or more steps or features may be added, omitted, combined, performed at a later time, etc.

Figure 2D:
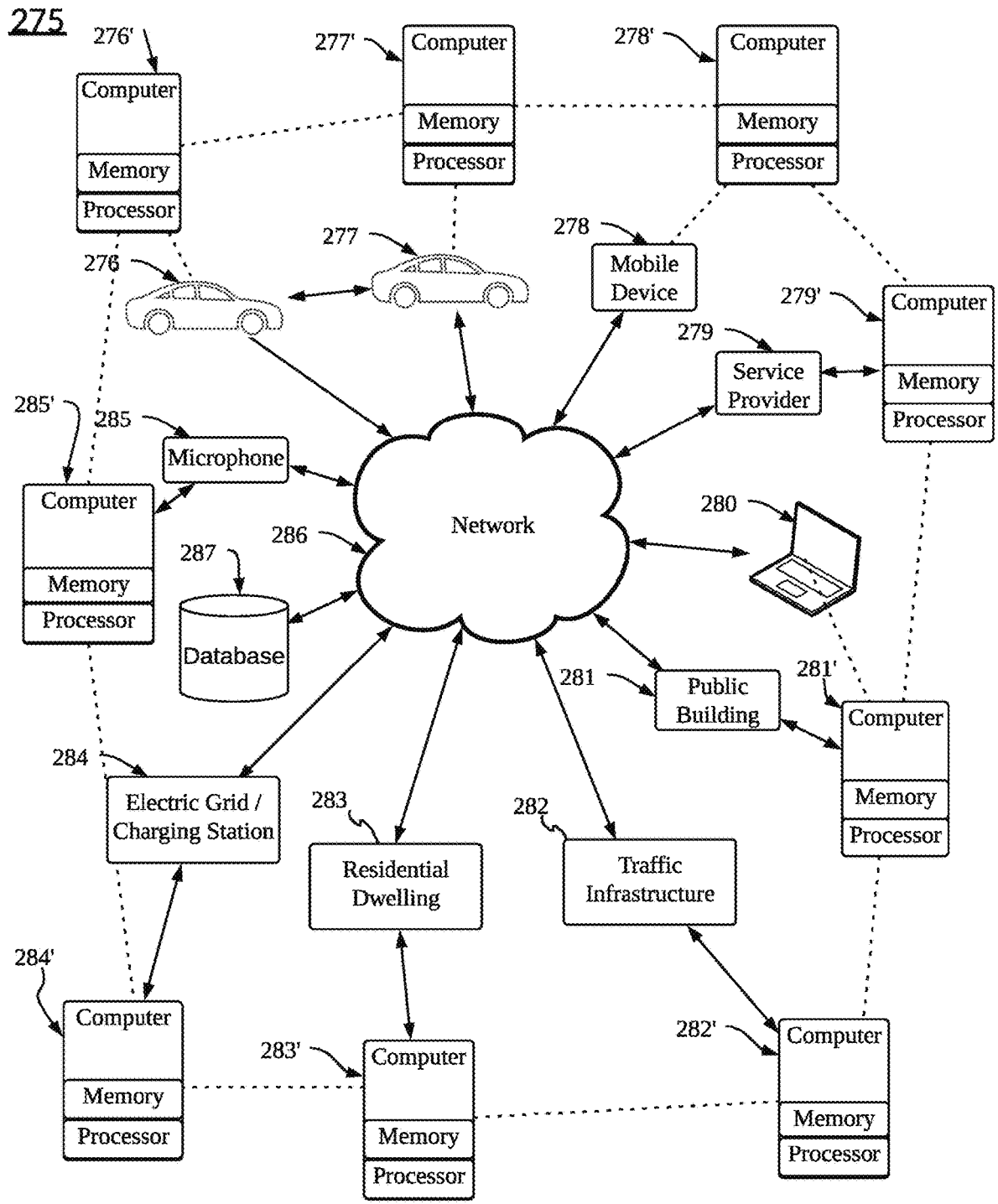
FIG. 2D illustrates interconnections between different elements, according to example embodiments.

FIG. 2D is a diagram showing interconnections between different elements 275. The instant solution may be stored and/or executed entirely or partially on and/or by one or more computing devices 278', 279', 281', 282', 283', 284', 276', 285', 287' and 277' associated with various entities, all communicably coupled and in communication with a network 286. A database 287 is communicably coupled to the network and allows for the storage and retrieval of data. In one embodiment, the database is an immutable ledger. One or more of the various entities may be a transport 276, one or more service provider 279, one or more public buildings 281, one or more traffic infrastructure 282, one or more residential dwellings 283, an electric grid/charging station 284, a microphone 285, and/or another transport 277. Other entities and/or devices, such as one or more private users using a smartphone 278, a laptop 280, and/or a wearable device may also interwork with the instant solution. The smartphone 278, laptop 280, the microphone 285, and other devices may be connected to one or more of the connected computing devices 278', 279', 281', 282', 283', 284', 276', 285', 287', and 277'. The one or more public buildings 281 may include various agencies. The one or more public buildings 281 may utilize a computing device 281'. The one or more service provider 279 may include a dealership, a tow truck service, a collision center or other repair shop. The one or more service provider 279 may utilize a computing apparatus 279'. These various computer devices may be directly and/or communicably coupled to one another such as via wired networks, wireless networks, blockchain networks, and the like. The microphone 285 may be utilized as a virtual assistant, in one embodiment. In one embodiment, the one or more traffic infrastructure 282 may include one or more traffic signals, one or more sensors including one or more cameras, vehicle speed sensors or traffic sensors, and/or other traffic infrastructure. The one or more traffic infrastructure 282 may utilize a computing device 282'.

In one embodiment, a transport 277/276 is capable of transporting a person, an object, a permanently or temporarily affixed apparatus, and the like. In one embodiment, the transport 277 may communicate with transport 276 via V2V communication, through the computers associated with each transport 276' and 277' and may be referred to as a transport, car, vehicle, automobile, and the like. The transport 276/277 may be a self-propelled wheeled conveyance, such as a car, a sports utility vehicle, a truck, a bus, a van, or other motor or battery-driven or fuel cell-driven transport. For example, transport 276/277 may be an electric vehicle, a hybrid vehicle, a hydrogen fuel cell vehicle, a plug-in hybrid vehicle, or any other type of vehicle that has a fuel cell stack, a motor, and/or a generator. Other examples of vehicles include bicycles, scooters, trains, planes, or boats, and any other form of conveyance that is capable of transportation. The transport 276/277 may be semi-autonomous or autonomous. For example, transport 276/277 may be self-maneuvering and navigate without human input. An autonomous vehicle may have and use one or more sensors and/or a navigation unit to drive autonomously.

In one embodiment, the solutions described and depicted herein can be utilized to determine an access to a transport via consensus of blockchain. In one embodiment, the solutions can also be utilized to perform profile validation before allowing an occupant to use a transport. In one embodiment, the solutions can also be utilized to have the transport indicate (visually, but also verbally in another embodiment, etc.) on or from the transport for an action the user needs to perform (that could be pre-recorded) and verify that it is the correct action. In one embodiment, the solutions can also be utilized to provide an ability to for a transport to determine, based on the risk level associated with data and driving environment, how to bifurcate the data and distribute a portion of the bifurcated data, with a lower risk level during a safe driving environment, to the occupant, and later distributing a remaining portion of the bifurcated data, with a higher risk level, to the occupant after the occupant has departed the transport. In one embodiment, the solutions can also be utilized to handle the transfer of a vehicle across boundaries (such as a country/state/etc.) through the use of blockchain and/or smart contracts and apply the rules of the new area to the vehicle.

In one embodiment, the solutions can also be utilized to allow a transport to continue to operate outside a boundary when a consensus is reached by the transport based on the operation of the transport and characteristics of an occupant of the transport. In one embodiment, the solutions can also be utilized to analyze the available data upload/download speed of a transport, size of the file and speed/direction the transport is traveling, to determine the distance needed to complete a data upload/download and assign a secure area boundary for the data upload/download to be executed. In one embodiment, the solutions can also be utilized to perform a normally dangerous maneuver in a safe manner, such as when the system determines that an exit is upcoming and when the transport is seemingly not prepared to exit (e.g. in the incorrect lane or traveling at a speed that is not conducive to making the upcoming exit) and instruct the subject transport as well as other proximate transports to allow the subject transport to exit in a safe manner. In one embodiment, the solutions can also be utilized to use one or more vehicles to validate diagnostics of another transport while both the one or more vehicles and the other transport are in motion.

In one embodiment, the solutions can also be utilized to detect lane usage at a location and time of day to either inform an occupant of a transport or direct the transport to recommend or not recommend a lane change. In one embodiment, the solutions can also be utilized to eliminate the need to send information through the mail and the need for a driver/occupant to respond by making a payment through the mail or in person. In one embodiment, the solutions can also be utilized to provide a service to an occupant of a transport, wherein the service provided is based on a subscription, and wherein the permission is acquired from other transports connected to the profile of the occupant. In one embodiment, the solutions can also be utilized to record changes in the condition of a rented object. In one embodiment, the solutions can also be utilized to seek a blockchain consensus from other transports that are in proximity to a damaged transport. In one embodiment, the solutions can also be utilized to receive media, from a server such as an insurance entity server, from the transport computer, which may be related to an accident. The server accesses one or more media files to access the damage to the transport and stores the damage assessment onto a blockchain. In one embodiment, the solutions can also be utilized to obtain a consensus to determine the severity of an event from a number of devices over various times prior to the event related to a transport.

In one embodiment, the solutions can also be utilized to solve a problem with a lack of video evidence for transport-related accidents. The current solution details the querying of media, by the transport involved in the accident, related to the accident from other transports that may have been proximate to the accident. In one embodiment, the solutions can also be utilized to utilize transports and other devices (for example, a pedestrian's cell phone, a streetlight camera, etc.) to record specific portions of a damaged transport.

In one embodiment, the solutions can also be utilized to warn an occupant when a transport is navigating toward a dangerous area and/or event, allowing for a transport to notify occupants or a central controller of a potentially dangerous area on or near the current transport route. In one embodiment, the solutions can also be utilized to detect when a transport traveling at a high rate of speed, at least one other transport is used to assist in slowing down the transport in a manner that minimally affects traffic. In one embodiment, the solutions can also be utilized to identify a dangerous driving situation where media is captured by the vehicle involved in the dangerous driving situation. A geofence is established based on the distance of the dangerous driving situation, and additional media is captured by at least one other vehicle within the established geofence. In one embodiment, the solutions can also be utilized to send a notification to one or more occupants of a transport that that transport is approaching a traffic control marking on a road, then if a transport crosses a marking, receiving indications of poor driving from other, nearby transports. In one embodiment, the solutions can also be utilized to make a transport partially inoperable by (in certain embodiments), limiting speed, limiting the ability to be near another vehicle, limiting speed to a maximum, and allowing only a given number of miles allowed per time period.

In one embodiment, the solutions can also be utilized to overcome a need for reliance on software updates to correct issues with a transport when the transport is not being operated correctly. Through the observation of other transports on a route, a server will receive data from potentially multiple other transports observing an unsafe or incorrect operation of a transport. Through analysis, these observations may result in a notification to the transport when the data suggest an unsafe or incorrect operation. In one embodiment, the solutions can also be utilized to provide notification between a transport and a potentially dangerous situation involving a person external to the transport. In one embodiment, the solutions can also be utilized to send data to a server by devices either associated with an accident with a transport, or devices proximate to the accident. Based on the severity of the accident or near accident, the server notifies the senders of the data. In one embodiment, the solutions can also be utilized to provide recommendations for operating a transport to either a driver or occupant of a transport based on the analysis of data. In one embodiment, the solutions can also be utilized to establish a geo-fence associated with a physical structure and determining payment responsibility to the transport. In one embodiment, the solutions can also be utilized to coordinate the ability to drop off a vehicle at a location using both the current state at the location, and a proposed future state using navigation destinations of other vehicles. In one embodiment, the solutions can also be utilized to coordinate the ability to automatically arrange for the drop off of a vehicle at a location such as a transport rental entity.

In one embodiment, the solutions can also be utilized to move transport to another location based on a user's event. More particularly, the system tracks a user's device, and modifies the transport to be moved proximate to the user upon the conclusion of the original event, or a modified event. In one embodiment, the solutions can also be utilized to allow for the validation of available locations within an area through the existing transports within the area. The approximate time when a location may be vacated is also determined based on verifications from the existing transports. In one embodiment, the solutions can also be utilized to move a transport to closer parking spaces as one becomes available and the elapsed time since initially parking is less than the average time of the event. Furthermore, moving the transport to a final parking space when the event is completed or according to a location of a device associated with at least one occupant of the transport. In one embodiment, the solutions can also be utilized to plan for the parking prior to the upcoming crowd. The system interacts with the transport to offer some services at a less than full price and/or guide the transport to alternative parking locations based on a priority of the transport, increasing optimization of the parking situation before arriving.

In one embodiment, the solutions can also be utilized to sell fractional ownership in transports or in determining pricing and availability in ride-sharing applications. In one embodiment, the solutions can also be utilized to provide accurate and timely reports of dealership sales activities well beyond what is currently available. In one embodiment, the solutions can also be utilized to allow a dealership to request an asset over the blockchain. By using the blockchain, a consensus is obtained before any asset is moved. Additionally, the process is automated, and payment may be initiated over the blockchain. In one embodiment, the solutions can also be utilized to arrange agreements that are made with multiple entities (such as service centers) wherein a consensus is acquired, and an action performed (such as diagnostics). In one embodiment, the solutions can also be utilized to associate digital keys with multiple users. A first user may be the operator of the transport, and a second user is the responsible party for the transport. These keys are authorized by a server where the proximity of the keys are validated against the location of a service provider. In one embodiment, the solutions can also be utilized to determine a needed service on a transport destination. One or more service locations are located that are able to provide the needed service that is both within an area on route to the destination and has availability to perform the service. The navigation of the transport is updated with the determined service location. A smart contract is identified that contains a compensation value for the service, and a blockchain transaction is stored in a distributed ledger for the transaction.

In one embodiment, the solutions can also be utilized to interfacing a service provider transport with a profile of an occupant of a transport to determine services and goods which may be of interest to occupants in a transport. These services and goods are determined by an occupant's history and/or preferences. The transport then receives offers from the service provider transport and, in another embodiment, meets the transport to provide the service/good. In one embodiment, the solutions can also be utilized to detect a transport within a range and send a service offer to the transport (such as a maintenance offer, a product offer, or the like). An agreement is made between the system and the transport, and a service provider is selected by the system to provide the agreement. In one embodiment, the solutions can also be utilized to assign one or more transports as a roadway manager, where the roadway manager assists in the control of traffic. The roadway manager may generate a roadway indicator (such as lights, displays, sounds) to assist in the flow of traffic. In one embodiment, the solutions can also be utilized to alert a driver of a transport by a device, wherein the device may be the traffic light or near an intersection. The alert is sent upon an event, such as when a light turns green and the transport in the front of a list of transports does not move.

Figure 3A:
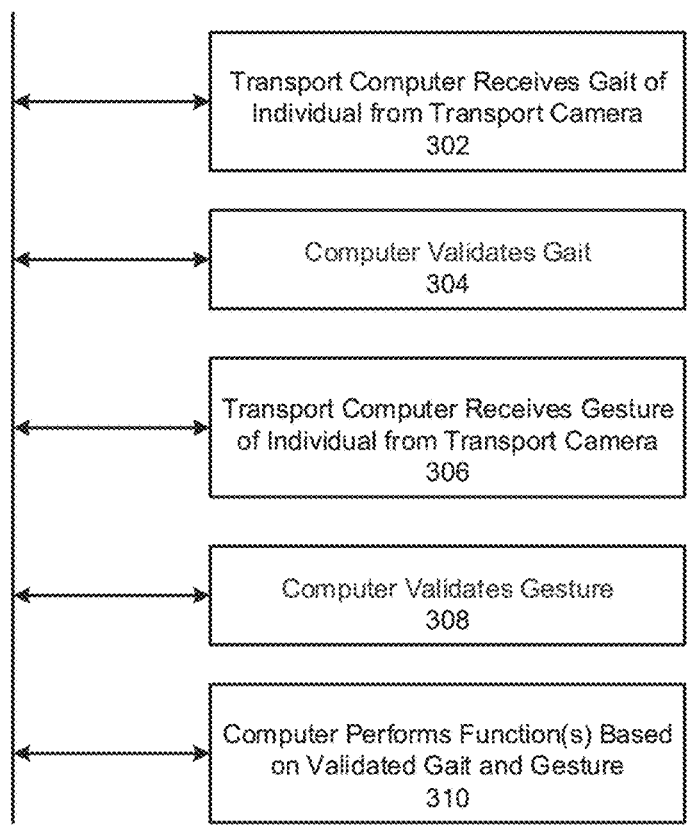
FIG. 3A illustrates a flow diagram, according to example embodiments.

FIG. 3A illustrates a flow diagram 300, according to example embodiments. Referring to FIG. 3A, the process includes one or more of the following steps. At block 302, a transport computer receives a gait of an individual 120 from a transport camera 108. At block 304, the computer validates the gait 120. At block 306, the transport computer receives a gesture of the individual 124 from the transport camera 108. At block 308, the computer validates the gesture 124. At block 310, the computer performs one or more functions based on the validated gait 120 and gesture 124.

Figure 3B:
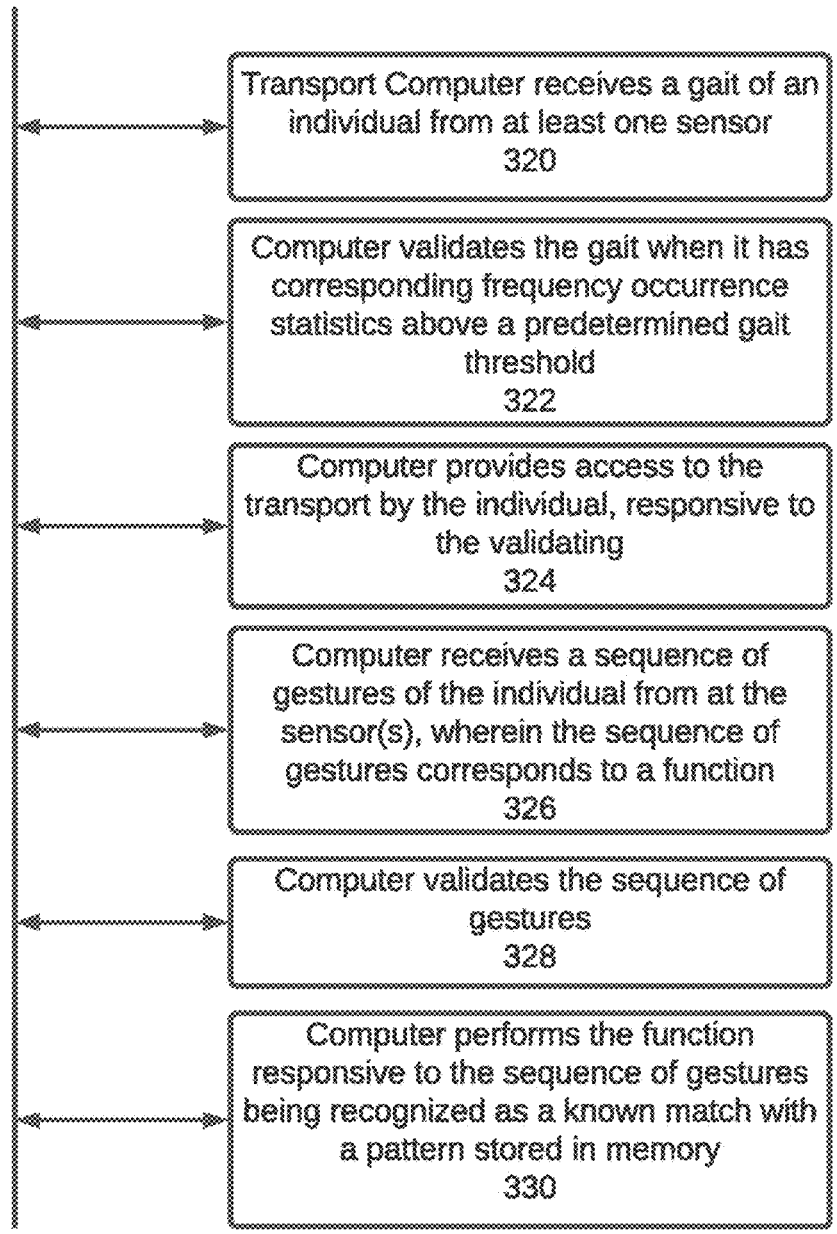
FIG. 3B illustrates another flow diagram, according to example embodiments.

FIG. 3B illustrates another flow diagram 318, according to example embodiments. Referring to FIG. 3B, the process includes one or more of the following steps. At block 320, a transport computer receives a gait of an individual from at least one sensor 320. At block 322, the computer validates the gait when it has corresponding frequency occurrence statistics above a predetermined gait threshold. At block 324, the computer provides access to the transport by the individual, responsive to the validating. At block 326, the computer receives a sequence of gestures of the individual from at the sensor(s), wherein the sequence of gestures corresponds to a function. At block 328, the computer validates the sequence of gestures. At block 330, the computer performs the function responsive to the sequence of gestures being recognized as a known match with a pattern stored in memory.

Figure 4:
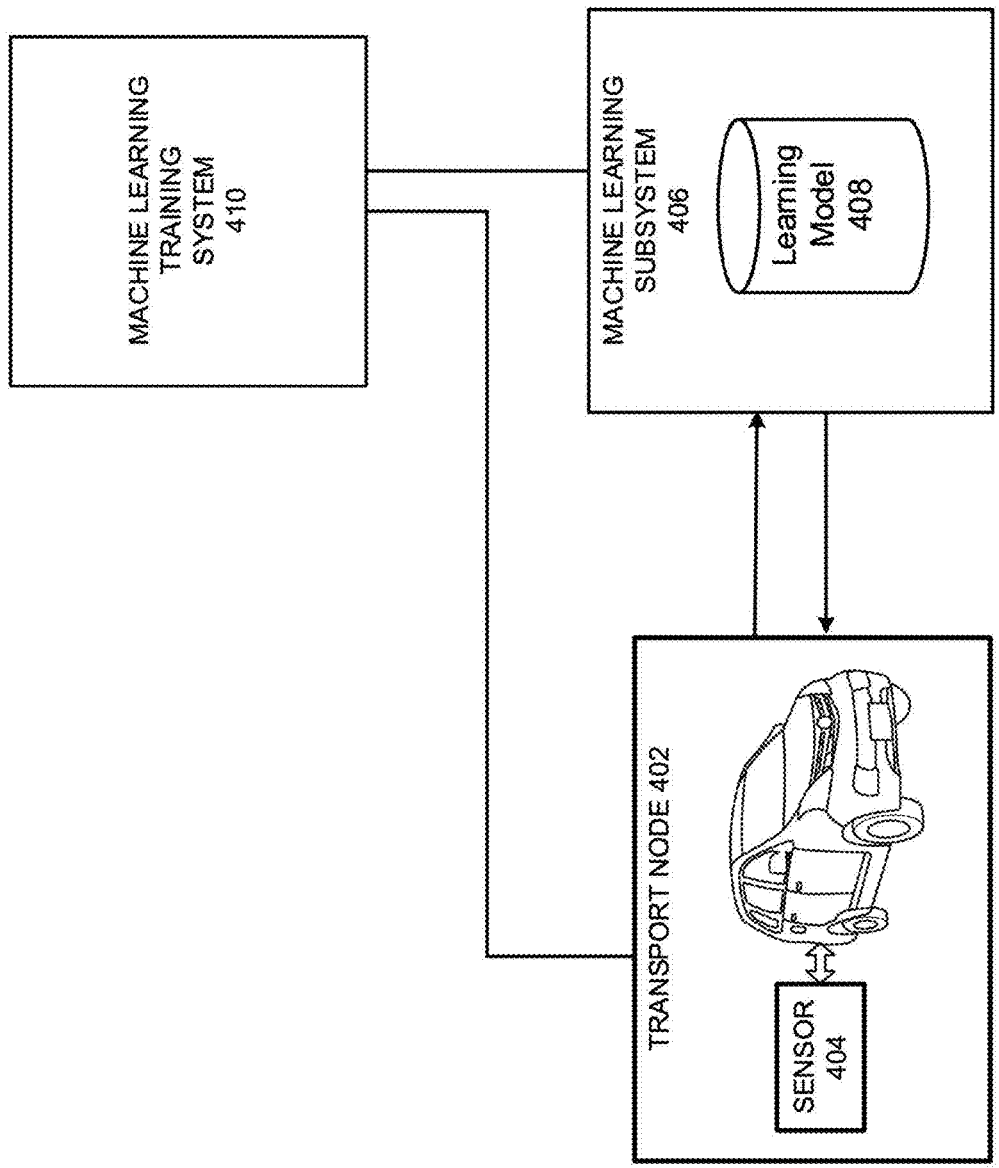
FIG. 4 illustrates a machine learning transport network diagram, according to example embodiments.

FIG. 4A illustrates a machine learning transport network diagram 400, according to example embodiments. The network 400 includes a transport node 402 that interfaces with a machine learning subsystem 406. The transport node includes one or more sensors 404.

The machine learning subsystem 406 contains a learning model 408 which is a mathematical artifact created by a machine learning training system 410 that generates predictions by finding patterns in one or more training data sets. In some embodiments, the machine learning subsystem 406 resides in the transport node 402. In other embodiments, the machine learning subsystem 406 resides outside of the transport node 402.

The transport node 402 sends data from the one or more sensors 404 to the machine learning subsystem 406. The machine learning subsystem 406 provides the one or more sensor 404 data to the learning model 408, which returns one or more predictions. The machine learning subsystem 406 sends one or more instructions to the transport node 402 based on the predictions from the learning model 408.

In a further embodiment, the transport node 402 may send the one or more sensor 404 data to the machine learning training system 410. In yet another embodiment, the machine learning subsystem 406 may sent the sensor 404 data to the machine learning subsystem 410. One or more of the applications, features, steps, solutions, etc., described and/or depicted herein may utilize the machine learning network 400 as described herein.

Figure 5A:
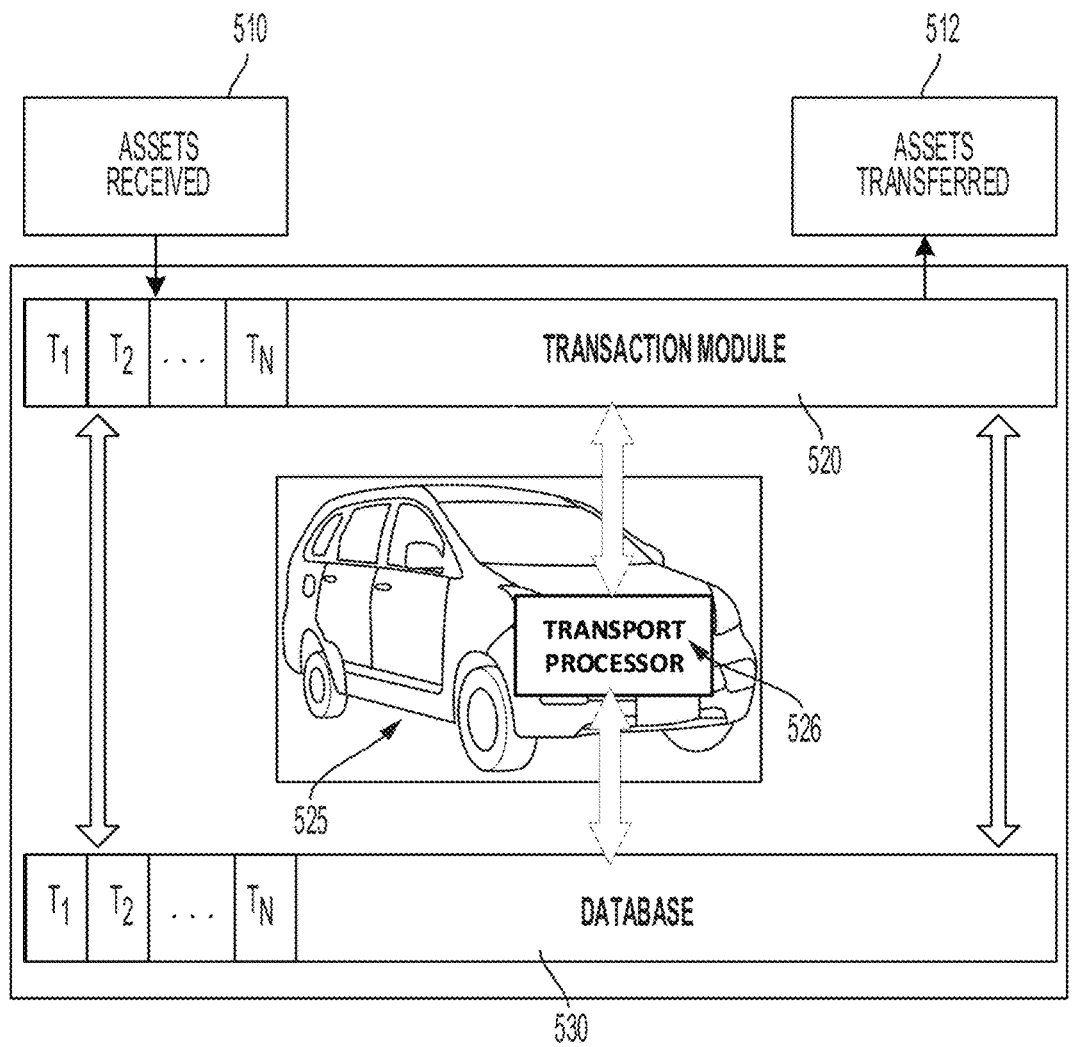
FIG. 5A illustrates an example vehicle configuration for managing database transactions associated with a vehicle, according to example embodiments.

FIG. 5A illustrates an example vehicle configuration 500 for managing database transactions associated with a vehicle, according to example embodiments. Referring to FIG. 5A, as a particular transport/vehicle 525 is engaged in transactions (e.g., vehicle service, dealer transactions, delivery/pickup, transportation services, etc.), the vehicle may receive assets 510 and/or expel/transfer assets 512 according to a transaction(s). A transport processor 526 resides in the vehicle 525 and communication exists between the transport processor 526, a database 530, a transport processor 526 and the transaction module 520. The transaction module 520 may record information, such as assets, parties, credits, service descriptions, date, time, location, results, notifications, unexpected events, etc. Those transactions in the transaction module 520 may be replicated into a database 530. The database 530 can be one of a SQL database, an RDBMS, a relational database, a non-relational database, a blockchain, a distributed ledger, and may be on board the transport, may be off board the transport, may be accessible directly and/or through a network, or be accessible to the transport.

Figure 5B:
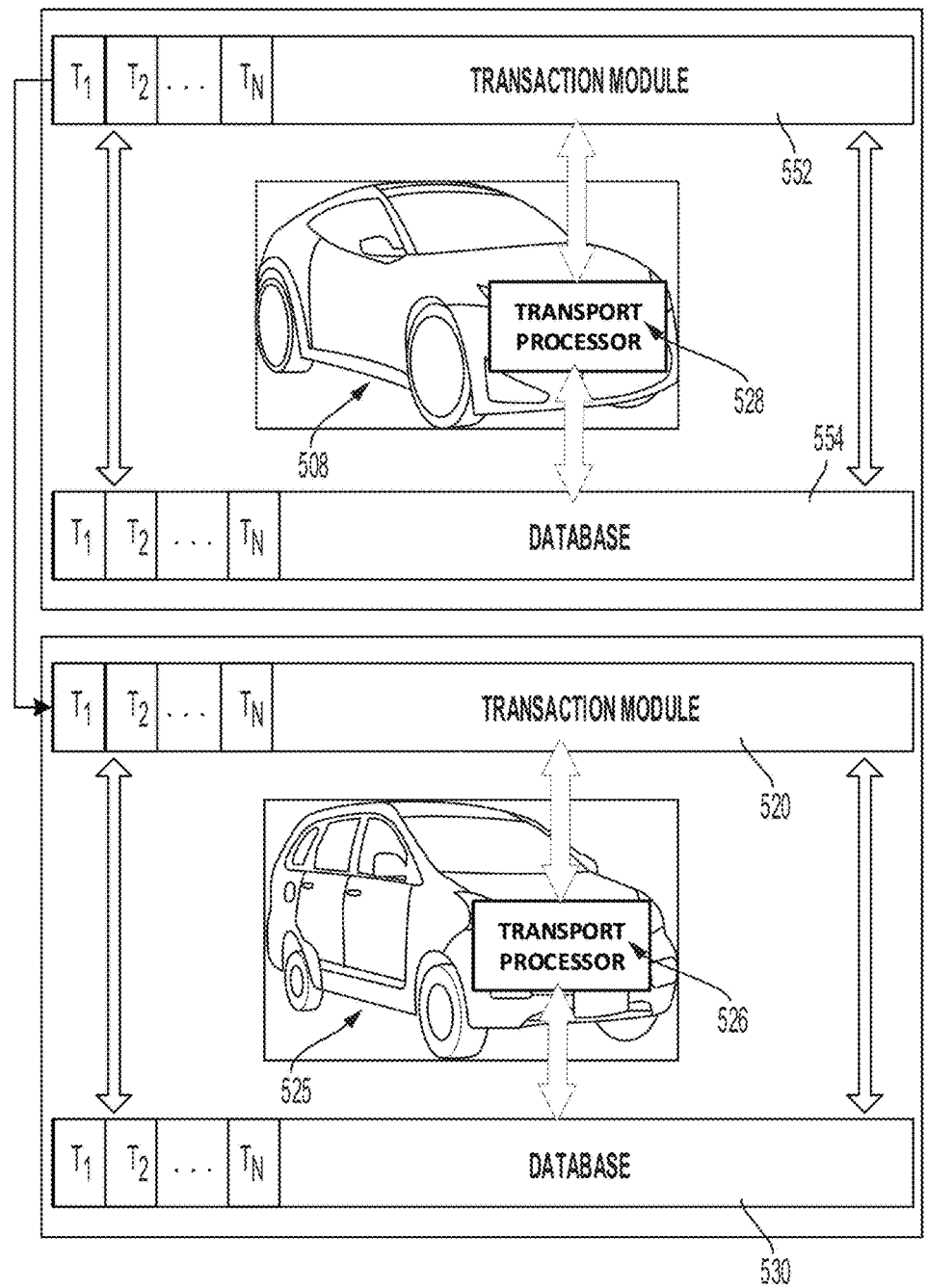
FIG. 5B illustrates another example vehicle configuration for managing database transactions conducted among various vehicles, according to example embodiments.

FIG. 5B illustrates an example vehicle configuration 550 for managing database transactions conducted among various vehicles, according to example embodiments. The vehicle 525 may engage with another vehicle 508 to perform various actions such as to share, transfer, acquire service calls, etc. when the vehicle has reached a status where the services need to be shared with another vehicle. For example, the vehicle 508 may be due for a battery charge and/or may have an issue with a tire and may be in route to pick up a package for delivery. A transport processor 528 resides in the vehicle 508 and communication exists between the transport processor 528, a database 554, a transport processor 528 and the transaction module 552. The vehicle 508 may notify another vehicle 525 which is in its network, and which operates on its blockchain member service. A transport processor 526 resides in the vehicle 525 and communication exists between the transport processor 526, a database 530, the transport processor 526 and a transaction module 520. The vehicle 525 may then receive the information via a wireless communication request to perform the package pickup from the vehicle 508 and/or from a server (not shown). The transactions are logged in the transaction modules 552 and 520 of both vehicles. The credits are transferred from vehicle 508 to vehicle 525 and the record of the transferred service is logged in the database 530/554 assuming that the blockchains are different from one another, or, are logged in the same blockchain used by all members. The database 554 can be one of a SQL database, an RDBMS, a relational database, a non-relational database, a blockchain, a distributed ledger, and may be on board the transport, may be off board the transport, may be accessible directly and/or through a network.

Figure 6A:
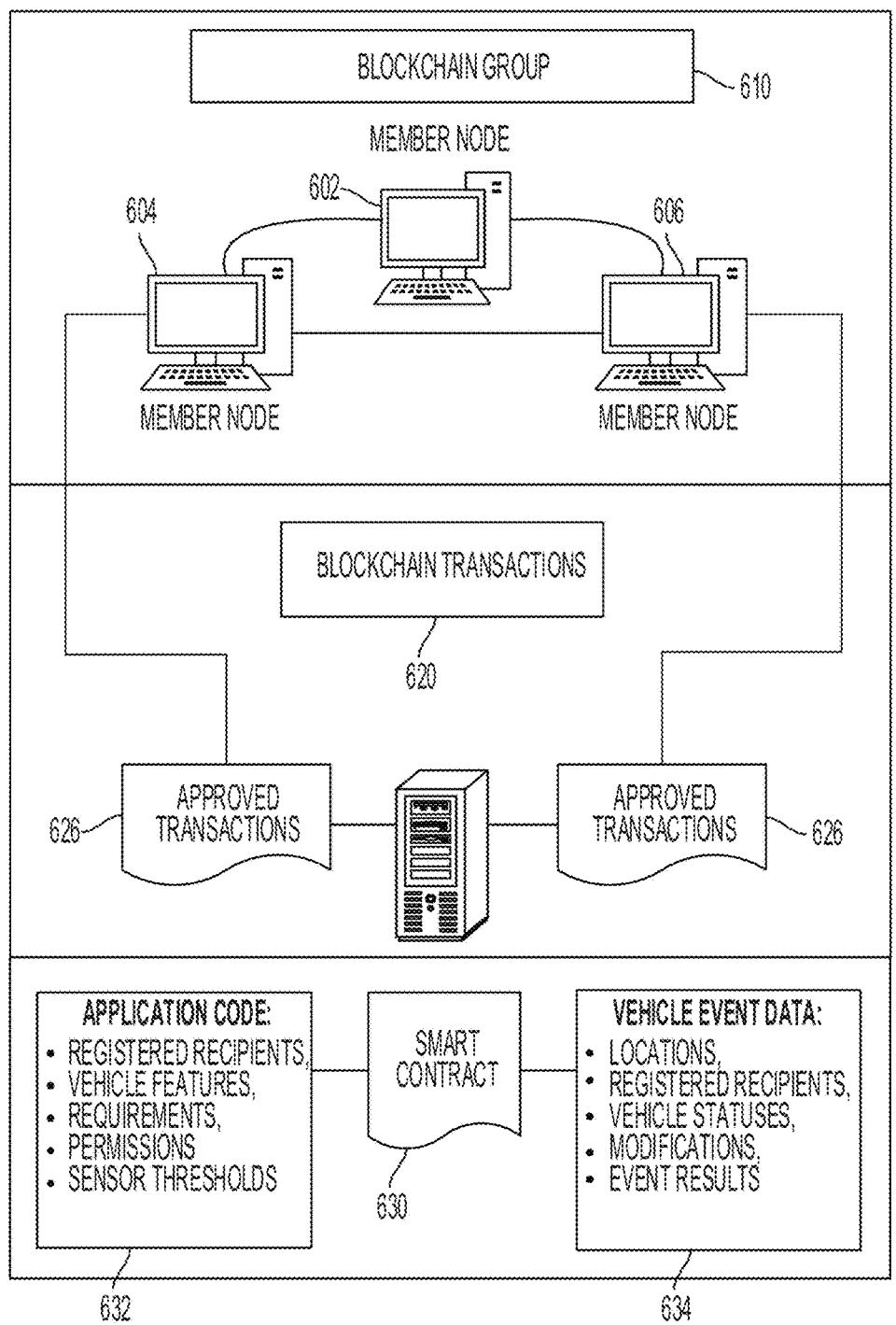
FIG. 6A illustrates a blockchain architecture configuration, according to example embodiments.

FIG. 6A illustrates a blockchain architecture configuration 600, according to example embodiments. Referring to FIG. 6A, the blockchain architecture 600 may include certain blockchain elements, for example, a group of blockchain member nodes 602-606 as part of a blockchain group 610. In one example embodiment, a permissioned blockchain is not accessible to all parties but only to those members with permissioned access to the blockchain data. The blockchain nodes participate in several activities, such as blockchain entry addition and validation process (consensus). One or more of the blockchain nodes may endorse entries based on an endorsement policy and may provide an ordering service for all blockchain nodes. A blockchain node may initiate a blockchain action (such as an authentication) and seek to write to a blockchain immutable ledger stored in the blockchain, a copy of which may also be stored on the underpinning physical infrastructure.

The blockchain transactions 620 are stored in memory of computers as the transactions are received and approved by the consensus model dictated by the members' nodes. Approved transactions 626 are stored in current blocks of the blockchain and committed to the blockchain via a committal procedure which includes performing a hash of the data contents of the transactions in a current block and referencing a previous hash of a previous block. Within the blockchain, one or more smart contracts 630 may exist that define the terms of transaction agreements and actions included in smart contract executable application code 632, such as registered recipients, vehicle features, requirements, permissions, sensor thresholds, etc. The code may be configured to identify whether requesting entities are registered to receive vehicle services, what service features they are entitled/required to receive given their profile statuses and whether to monitor their actions in subsequent events. For example, when a service event occurs and a user is riding in the vehicle, the sensor data monitoring may be triggered and a certain parameter, such as a vehicle charge level, may be identified as being above/below a particular threshold for a particular period of time, then the result may be a change to a current status which requires an alert to be sent to the managing party (i.e., vehicle owner, vehicle operator, server, etc.) so the service can be identified and stored for reference. The vehicle sensor data collected may be based on types of sensor data used to collect information about vehicle's status. The sensor data may also be the basis for the vehicle event data 634, such as a location(s) to be traveled, an average speed, a top speed, acceleration rates, whether there were any collisions, was the expected route taken, what is the next destination, whether safety measures are in place, whether the vehicle has enough charge/fuel, etc. All such information may be the basis of smart contract terms 630, which are then stored in a blockchain. For example, sensor thresholds stored in the smart contract can be used as the basis for whether a detected service is necessary and when and where the service should be performed.

Figure 6B:
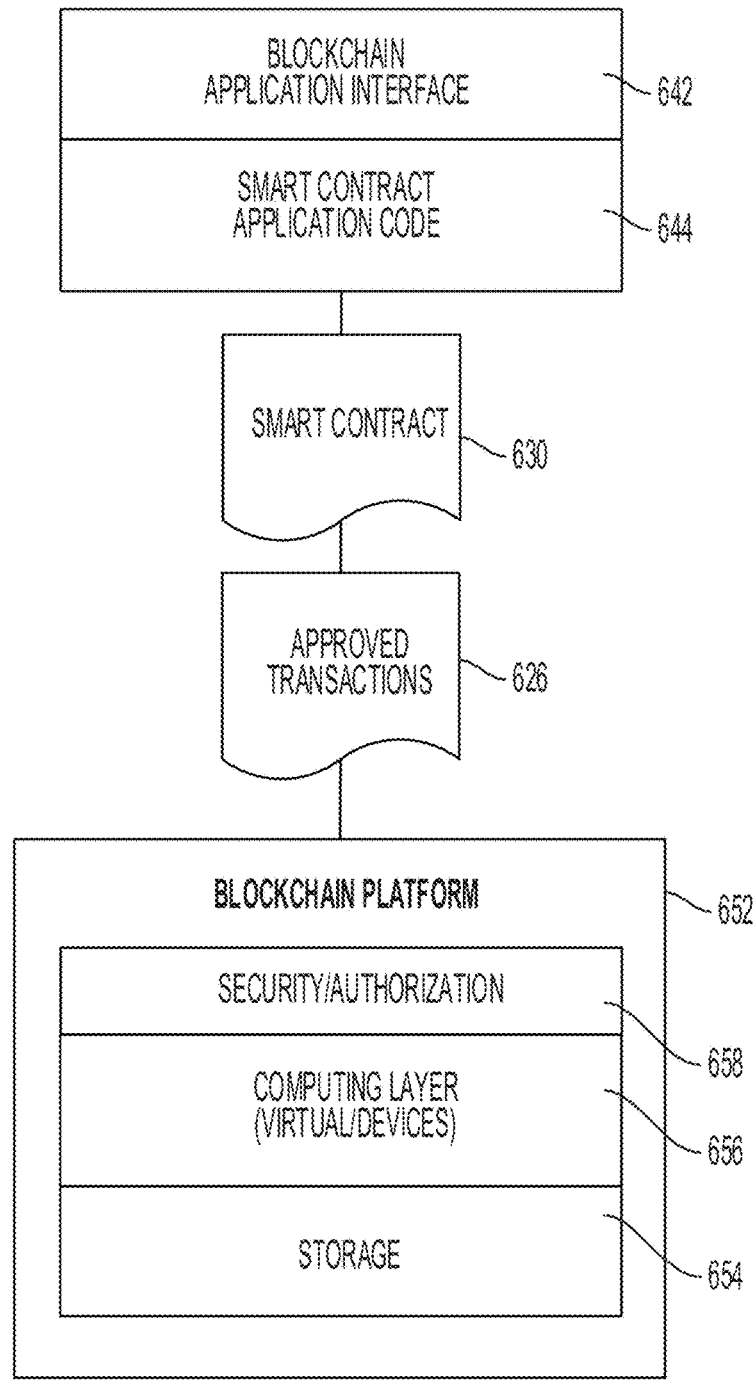
FIG. 6B illustrates another blockchain configuration, according to example embodiments.

FIG. 6B illustrates a shared ledger configuration, according to example embodiments. Referring to FIG. 6B, the blockchain logic example 640 includes a blockchain application interface 642 as an API or plug-in application that links to the computing device and execution platform for a particular transaction. The blockchain configuration 640 may include one or more applications which are linked to application programming interfaces (APIs) to access and execute stored program/application code (e.g., smart contract executable code, smart contracts, etc.) which can be created according to a customized configuration sought by participants and can maintain their own state, control their own assets, and receive external information. This can be deployed as an entry and installed, via appending to the distributed ledger, on all blockchain nodes.

The smart contract application code 644 provides a basis for the blockchain transactions by establishing application code which when executed causes the transaction terms and conditions to become active. The smart contract 630, when executed, causes certain approved transactions 626 to be generated, which are then forwarded to the blockchain platform 652. The platform includes a security/authorization 658, computing devices which execute the transaction management 656 and a storage portion 654 as a memory that stores transactions and smart contracts in the blockchain.

The blockchain platform may include various layers of blockchain data, services (e.g., cryptographic trust services, virtual execution environment, etc.), and underpinning physical computer infrastructure that may be used to receive and store new entries and provide access to auditors which are seeking to access data entries. The blockchain may expose an interface that provides access to the virtual execution environment necessary to process the program code and engage the physical infrastructure. Cryptographic trust services may be used to verify entries such as asset exchange entries and keep information private.

The blockchain architecture configuration of FIGS. 6A and 6B may process and execute program/application code via one or more interfaces exposed, and services provided, by the blockchain platform. As a non-limiting example, smart contracts may be created to execute reminders, updates, and/or other notifications subject to the changes, updates, etc. The smart contracts can themselves be used to identify rules associated with authorization and access requirements and usage of the ledger. For example, the information may include a new entry, which may be processed by one or more processing entities (e.g., processors, virtual machines, etc.) included in the blockchain layer. The result may include a decision to reject or approve the new entry based on the criteria defined in the smart contract and/or a consensus of the peers. The physical infrastructure may be utilized to retrieve any of the data or information described herein.

Within smart contract executable code, a smart contract may be created via a high-level application and programming language, and then written to a block in the blockchain. The smart contract may include executable code which is registered, stored, and/or replicated with a blockchain (e.g., distributed network of blockchain peers). An entry is an execution of the smart contract code, which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment, then deleted once the data needed for the blockchain is identified.

A smart contract executable code may include the code interpretation of a smart contract, with additional features. As described herein, the smart contract executable code may be program code deployed on a computing network, where it is executed and validated by chain validators together during a consensus process. The smart contract executable code receives a hash and retrieves from the blockchain a hash associated with the data template created by use of a previously stored feature extractor. If the hashes of the hash identifier and the hash created from the stored identifier template data match, then the smart contract executable code sends an authorization key to the requested service. The smart contract executable code may write to the blockchain data associated with the cryptographic details.

Figure 6C:
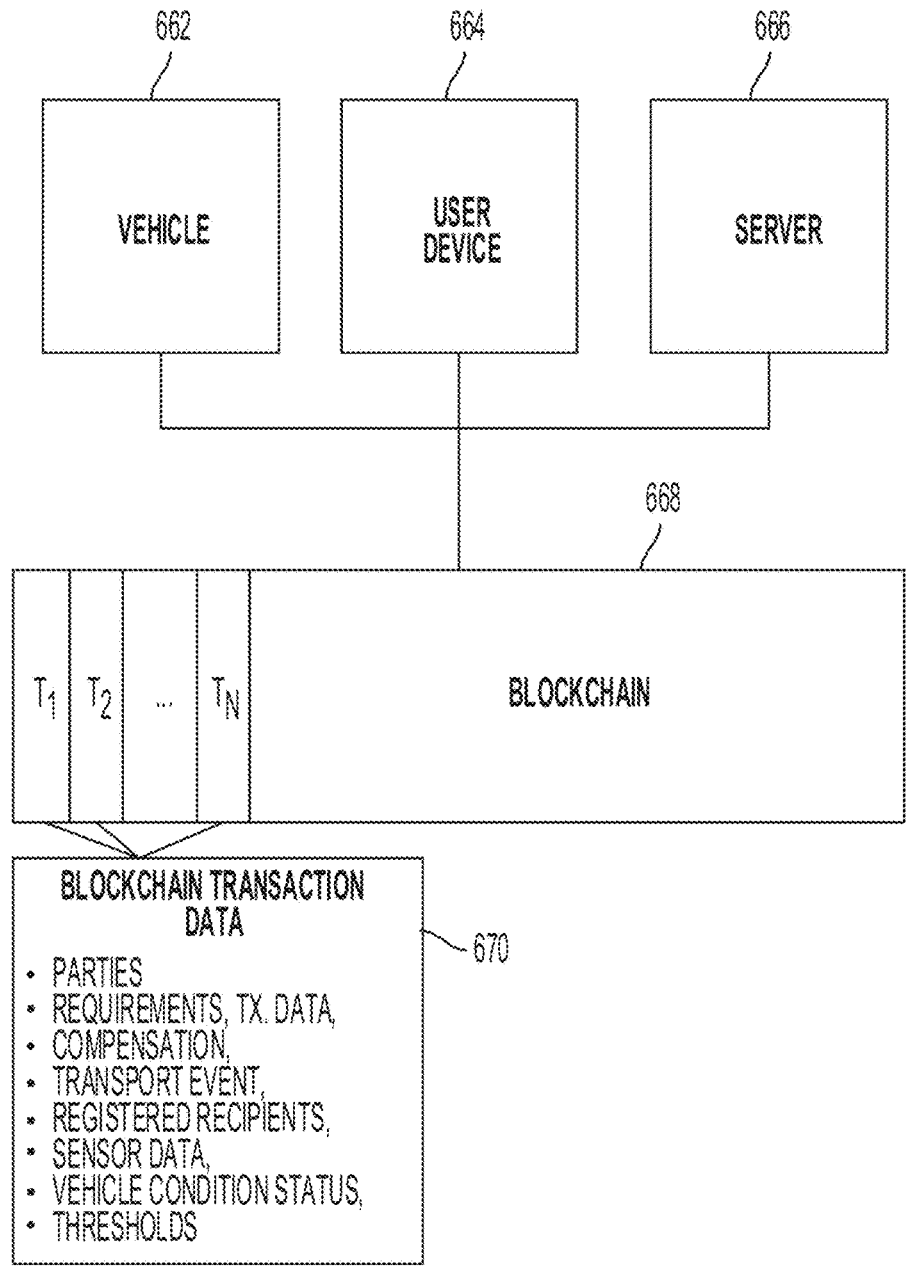
FIG. 6C illustrates a blockchain configuration for storing blockchain transaction data, according to example embodiments.

FIG. 6C illustrates a blockchain configuration for storing blockchain transaction data, according to example embodiments. Referring to FIG. 6C, the example configuration 660 provides for the vehicle 662, the user device 664 and a server 666 sharing information with a distributed ledger (i.e., blockchain) 668. The server may represent a service provider entity inquiring with a vehicle service provider to share user profile rating information in the event that a known and established user profile is attempting to rent a vehicle with an established rated profile. The server 666 may be receiving and processing data related to a vehicle's service requirements. As the service events occur, such as the vehicle sensor data indicates a need for fuel/charge, a maintenance service, etc., a smart contract may be used to invoke rules, thresholds, sensor information gathering, etc., which may be used to invoke the vehicle service event. The blockchain transaction data 670 is saved for each transaction, such as the access event, the subsequent updates to a vehicle's service status, event updates, etc. The transactions may include the parties, the requirements (e.g., 18 years of age, service eligible candidate, valid driver's license, etc.), compensation levels, the distance traveled during the event, the registered recipients permitted to access the event and host a vehicle service, rights/permissions, sensor data retrieved during the vehicle event operation to log details of the next service event and identify a vehicle's condition status, and thresholds used to make determinations about whether the service event was completed and whether the vehicle's condition status has changed.

Figure 6D:
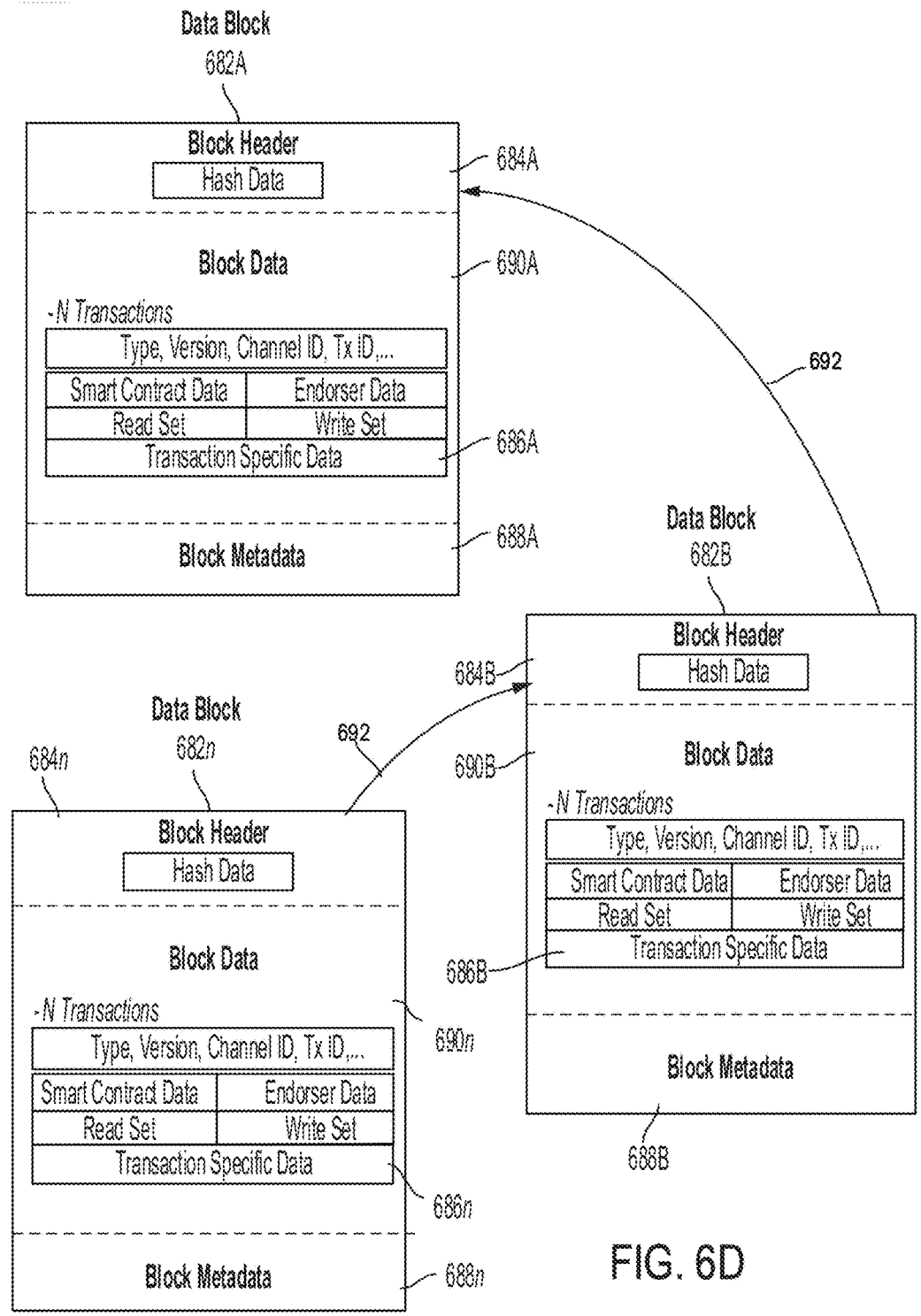
FIG. 6D illustrates example data blocks, according to example embodiments.

FIG. 6D illustrates blockchain blocks 680 that can be added to a distributed ledger, according to example embodiments, and contents of block structures 682A to 682n. Referring to FIG. 6D, clients (not shown) may submit entries to blockchain nodes to enact activity on the blockchain. As an example, clients may be applications that act on behalf of a requester, such as a device, person or entity to propose entries for the blockchain. The plurality of blockchain peers (e.g., blockchain nodes) may maintain a state of the blockchain network and a copy of the distributed ledger. Different types of blockchain nodes/peers may be present in the blockchain network including endorsing peers, which simulate and endorse entries proposed by clients and committing peers which verify endorsements, validate entries, and commit entries to the distributed ledger. In this example, the blockchain nodes may perform the role of endorser node, committer node, or both.

The instant system includes a blockchain which stores immutable, sequenced records in blocks, and a state database (current world state) maintaining a current state of the blockchain. One distributed ledger may exist per channel and each peer maintains its own copy of the distributed ledger for each channel of which they are a member. The instant blockchain is an entry log, structured as hash-linked blocks where each block contains a sequence of N entries. Blocks may include various components such as those shown in FIG. 6D. The linking of the blocks may be generated by adding a hash of a prior block's header within a block header of a current block. In this way, all entries on the blockchain are sequenced and cryptographically linked together preventing tampering with blockchain data without breaking the hash links. Furthermore, because of the links, the latest block in the blockchain represents every entry that has come before it. The instant blockchain may be stored on a peer file system (local or attached storage), which supports an append-only blockchain workload.

The current state of the blockchain and the distributed ledger may be stored in the state database. Here, the current state data represents the latest values for all keys ever included in the chain entry log of the blockchain. Smart contract executable code invocations execute entries against the current state in the state database. To make these smart contract executable code interactions extremely efficient, the latest values of all keys are stored in the state database. The state database may include an indexed view into the entry log of the blockchain, it can therefore be regenerated from the chain at any time. The state database may automatically get recovered (or generated if needed) upon peer startup before entries are accepted.

Endorsing nodes receive entries from clients and endorse the entry based on simulated results. Endorsing nodes hold smart contracts, which simulate the entry proposals. When an endorsing node endorses an entry, the endorsing nodes create an entry endorsement which is a signed response from the endorsing node to the client application indicating the endorsement of the simulated entry. The method of endorsing an entry depends on an endorsement policy, which may be specified within smart contract executable code. An example of an endorsement policy is "the majority of endorsing peers must endorse the entry." Different channels may have different endorsement policies. Endorsed entries are forward by the client application to an ordering service.

The ordering service accepts endorsed entries, orders them into a block, and delivers the blocks to the committing peers. For example, the ordering service may initiate a new block when a threshold of entries has been reached, a timer times out, or another condition. In this example, blockchain node is a committing peer that has received a data block 682A for storage on the blockchain. The ordering service may be made up of a cluster of orderers. The ordering service does not process entries, smart contracts, or maintain the shared ledger. Rather, the ordering service may accept the endorsed entries and specifies the order in which those entries are committed to the distributed ledger. The architecture of the blockchain network may be designed such that the specific implementation of 'ordering' (e.g., Solo, Kafka, BFT, etc.) becomes a pluggable component.

Entries are written to the distributed ledger in a consistent order. The order of entries is established to ensure that the updates to the state database are valid when they are committed to the network. Unlike a cryptocurrency blockchain system (e.g., Bitcoin, etc.) where ordering occurs through the solving of a cryptographic puzzle, or mining, in this example the parties of the distributed ledger may choose the ordering mechanism that best suits that network.

Referring to FIG. 6D, a block 682A (also referred to as a data block) that is stored on the blockchain and/or the distributed ledger may include multiple data segments such as a block header 684A to 684n, transaction specific data 686A to 686n, and block metadata 688A to 688n. It should be appreciated that the various depicted blocks and their contents, such as block 682A and its contents are merely for purposes of an example and are not meant to limit the scope of the example embodiments. In some cases, both the block header 684A and the block metadata 688A may be smaller than the transaction specific data 686A which stores entry data; however, this is not a requirement. The block 682A may store transactional information of N entries (e.g., 100, 500, 1000, 2000, 3000, etc.) within the block data 690A to 690n. The block 682A may also include a link to a previous block (e.g., on the blockchain) within the block header 684A. In particular, the block header 684A may include a hash of a previous block's header. The block header 684A may also include a unique block number, a hash of the block data 690A of the current block 682A, and the like. The block number of the block 682A may be unique and assigned in an incremental/sequential order starting from zero. The first block in the blockchain may be referred to as a genesis block, which includes information about the blockchain, its members, the data stored therein, etc.

The block data 690A may store entry information of each entry that is recorded within the block. For example, the entry data may include one or more of a type of the entry, a version, a timestamp, a channel ID of the distributed ledger, an entry ID, an epoch, a payload visibility, a smart contract executable code path (deploy tx), a smart contract executable code name, a smart contract executable code version, input (smart contract executable code and functions), a client (creator) identify such as a public key and certificate, a signature of the client, identities of endorsers, endorser signatures, a proposal hash, smart contract executable code events, response status, namespace, a read set (list of key and version read by the entry, etc.), a write set (list of key and value, etc.), a start key, an end key, a list of keys, a Merkel tree query summary, and the like. The entry data may be stored for each of the N entries.

In some embodiments, the block data 690A may also store transaction specific data 686A which adds additional information to the hash-linked chain of blocks in the blockchain. Accordingly, the data 686A can be stored in an immutable log of blocks on the distributed ledger. Some of the benefits of storing such data 686A are reflected in the various embodiments disclosed and depicted herein. The block metadata 688A may store multiple fields of metadata (e.g., as a byte array, etc.). Metadata fields may include signature on block creation, a reference to a last configuration block, an entry filter identifying valid and invalid entries within the block, last offset persisted of an ordering service that ordered the block, and the like. The signature, the last configuration block, and the orderer metadata may be added by the ordering service. Meanwhile, a committer of the block (such as a blockchain node) may add validity/invalidity information based on an endorsement policy, verification of read/write sets, and the like. The entry filter may include a byte array of a size equal to the number of entries in the block data 690A and a validation code identifying whether an entry was valid/invalid.

The other blocks 682B to 682n in the blockchain also have headers, files, and values. However, unlike the first block 682A, each of the headers 684A to 684n in the other blocks includes the hash value of an immediately preceding block. The hash value of the immediately preceding block may be just the hash of the header of the previous block or may be the hash value of the entire previous block. By including the hash value of a preceding block in each of the remaining blocks, a trace can be performed from the Nth block back to the genesis block (and the associated original file) on a block-by-block basis, as indicated by arrows 692, to establish an auditable and immutable chain-of-custody.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 7 illustrates an example computer system architecture 700, which may represent or be integrated in any of the above-described components, etc.

Figure 7:
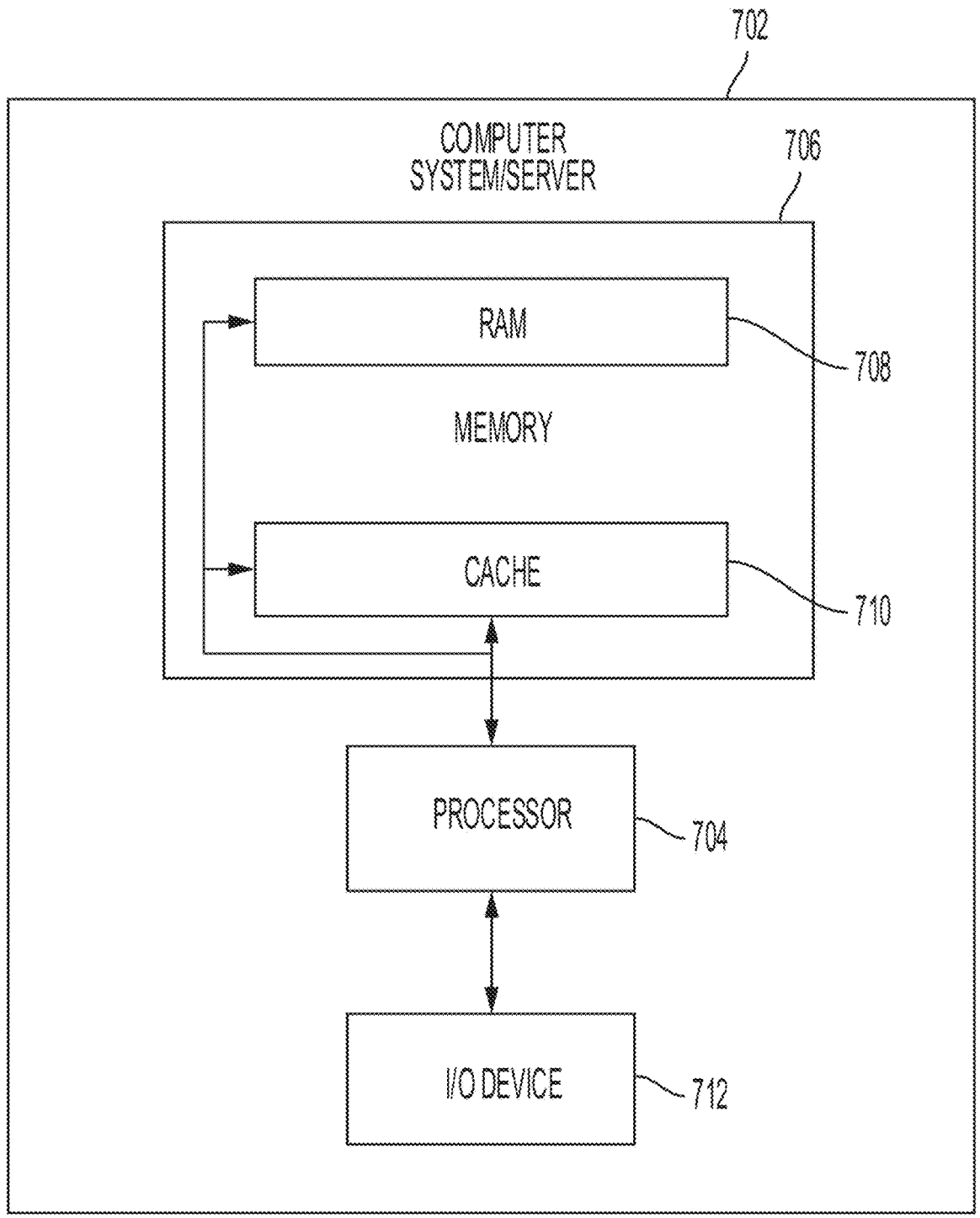
FIG. 7 illustrates an example system that supports one or more of the example embodiments.

FIG. 7 is not intended to suggest any limitation as to the scope of use or functionality of embodiments of the application described herein. Regardless, the computing node 700 is capable of being implemented and/or performing any of the functionality set forth hereinabove.

In computing node 700 there is a computer system/server 702, which is operational with numerous other general purpose or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 708 and/or cache memory 710. Computer system/server 702 may further include other removable/non-removable, volatile/non-volatile computer system storage media. By way of example only, memory 706 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 706 may include at least one program product having a set (e.g., at least one) of program modules that are configured to carry out the functions of various embodiments of the application.

Program/utility, having a set (at least one) of program modules, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 702 may also communicate with one or more external devices via an I/O device 712 (such as an I/O adapter), which may include a keyboard, a pointing device, a display, a voice recognition module, etc., one or more devices that enable a user to interact with computer system/server 702, and/or any devices (e.g., network card, modem, etc.) that enable computer system/server 702 to communicate with one or more other computing devices. Such communication can occur via I/O interfaces of the device 712. Still yet, computer system/server 702 can communicate with one or more networks such as a local area network (LAN), a general wide area network (WAN), and/or a public network (e.g., the Internet) via a network adapter. As depicted, device 712 communicates with the other components of computer system/server 702 via a bus. It should be understood that although not shown, other hardware and/or software components could be used in conjunction with computer system/server 702. Examples, include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms etc.) thereto.

What is claimed is:

1. A method, comprising:
    receiving, by a computer associated with a transport, a gait of an individual from at least one sensor associated with the transport;
    validating, by the computer, the gait when the gait has corresponding frequency occurrence statistics above a predetermined gait threshold;
    responsive to the validating, providing, by the computer, access to the transport by the individual;
    receiving, by the computer, a sequence of gestures of the individual from the at least one sensor, wherein the sequence of gestures corresponds to a function;
    validating, by the computer, the sequence of gestures; and
    responsive to the validating, performing, by the computer, the function responsive to the sequence of gestures being recognized as a known match with a pattern stored in memory.

2. The method of claim 1, wherein the determining of the gait comprises one or more of:
    analyzing motion of the individual, a pace of the individual, leg movement of the individual, torso movement of the individual, arm movement of the individual, and head movement of the individual.

3. The method of claim 1, wherein the sequence of gestures is provided in response to an indication by the transport to the individual, the indication comprising at least one of:
    flashing one or more lights of the transport;
    transmitting an audible message or tone from the transport to the individual; and
    providing a notification to a device associated with the individual.

4. The method of claim 1, comprising:
    receiving, by a device associated with the individual, the sequence of gestures; and
    sending, by the device, the sequence of gestures to the transport.

5. The method of claim 1, wherein the function is comprised of one or more of unlocking a transport door, starting an engine of the transport, utilizing a transport heater or air conditioner, utilizing a transport entertainment system, and a summon function of the transport.

6. The method of claim 1, wherein the sequence of gestures enables a sequence of functions of the transport.

7. The method of claim 1, comprising:
    receiving, by a server, one or more of the validated gait and the validated sequence of gestures; and
    providing, by the server, access to another structure, based on the receiving.

8. A system, comprising:
    a processor of a computer associated with a transport; a memory on which are stored machine-readable instructions that when executed by the processor, cause the processor to:
    receive a gait of an individual from at least one sensor associated with the transport;
    validate the gait when the gait has corresponding frequency occurrence statistics above a predetermined gait threshold;
    responsive to the validate, provide access to the transport by the individual;
    receive a sequence of gestures of the individual from at the at least one sensor, wherein the sequence of gestures corresponds to a function;
    validate the sequence of gestures; and
    responsive to the validate, perform the function responsive to the sequence of gestures are recognized as a known match with a pattern stored in memory.

9. The system of claim 8, wherein the determine of the gait comprises one or more of:
    analyze motion of the individual, a pace of the individual, leg movement of the individual, torso movement of the individual, arm movement of the individual, and head movement of the individual.

10. The system of claim 8, wherein the sequence of gestures is provided in response to an indication by the transport to the individual, the indication comprising at least one of:
    flashing one or more lights of the transport;

transmit an audible message or tone from the transport to the individual; and provide a notification to a device associated with the individual.

11. The system of claim 8, comprising:

receive, by a device associated with the individual, the sequence of gestures; and send, by the device, the sequence of gestures to the transport.

12. The system of claim 8, wherein the function is comprised of one or more of unlock a transport door, start an engine of the transport, utilize a transport heater or air conditioner, utilize a transport entertainment system, and a summon function of the transport.

13. The system of claim 8, wherein the sequence of gestures enables a sequence of functions of the transport.

14. The system of claim 8, comprising:

receive, by a server, one or more of the validated gait and the validated sequence of gestures; and provide, by the server, access to another structure, based on the receiving.

15. A non-transitory computer readable medium comprising instructions, that when read by a processor, cause the processor to perform:

receiving, by a computer associated with a transport, a gait of an individual from at least one sensor associated with the transport;

validating, by the computer, the gait when the gait has corresponding frequency occurrence statistics above a predetermined gait threshold;

responsive to the validating, providing, by the computer, access to the transport by the individual;

receiving, by the computer, a sequence of gestures of the individual from at the at least one sensor, wherein the sequence of gestures corresponds to a function;

validating, by the computer, the sequence of gestures; and responsive to the validating, performing, by the computer, the function responsive to the sequence of gestures being recognized as a known match with a pattern stored in memory.

16. The non-transitory computer readable medium of claim 15, wherein the determining of the gait comprises one or more of:

analyzing motion of the individual, a pace of the individual, leg movement of the individual, torso movement of the individual, arm movement of the individual, and head movement of the individual.

17. The non-transitory computer readable medium of claim 15, wherein the sequence of gestures is provided in response to an indication by the transport to the individual, the indication comprising at least one of:

flashing one or more lights of the transport;

transmitting an audible message or tone from the transport to the individual; and providing a notification to a device associated with the individual.

18. The non-transitory computer readable medium of claim 15, comprising:

receiving, by a device associated with the individual, the sequence of gestures; and sending, by the device, the sequence of gestures to the transport.

19. The non-transitory computer readable medium of claim 15, wherein the sequence of gestures enables a sequence of functions of the transport.

20. The non-transitory computer readable medium of claim 15, comprising:

receiving, by a server, one or more of the validated gait and the validated sequence of gestures; and providing, by the server, access to another structure, based on the receiving.

* * * * *